(12) United States Patent
Gardner et al.

(10) Patent No.: US 9,182,280 B1
(45) Date of Patent: Nov. 10, 2015

(54) METHOD FOR REDUCING FREQUENCY OF TAKING BACKGROUND/REFERENCE SPECTRA IN FTIR OR FTIR-ATR SPECTROSCOPY AND HANDHELD MEASUREMENT DEVICE EMBODYING SAME

(71) Applicant: Thermo Scientific Portable Analytical Instruments Inc., Tewksbury, MA (US)

(72) Inventors: Craig M. Gardner, Belmont, MA (US); Michael Burka, Winchester, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 0 days.

(21) Appl. No.: 14/455,212

(22) Filed: Aug. 8, 2014

(51) Int. Cl.
*G01N 21/35* (2014.01)
*G01J 3/02* (2006.01)

(52) U.S. Cl.
CPC ............... *G01J 3/0297* (2013.01); *G01N 21/35* (2013.01); *G01N 2021/3595* (2013.01); *G01N 2201/06113* (2013.01); *G01N 2201/1242* (2013.01)

(58) Field of Classification Search
CPC ............. G01N 21/552; G01N 2021/3595; G01N 21/359; G01N 21/35
USPC .................................................. 250/339.08
See application file for complete search history.

(56) References Cited

U.S. PATENT DOCUMENTS

| | | | |
|---|---|---|---|
| 5,020,909 A * | 6/1991 | Landa | 356/300 |
| 5,489,980 A * | 2/1996 | Anthony | 356/308 |
| 8,248,588 B2 | 8/2012 | Azimi et al. | |
| 2004/0034480 A1 * | 2/2004 | Binder | 702/24 |
| 2009/0101524 A1 * | 4/2009 | Woodward et al. | 205/787.5 |

* cited by examiner

*Primary Examiner* — Marcus Taningco
(74) *Attorney, Agent, or Firm* — John C. Abraham

(57) ABSTRACT

Featured is a method for reducing frequency of taking background spectra in FTIR or FTIR-ATR spectroscopy. Such a method includes determining if there is a pre-existing reference spectrum available and if such a reference spectrum is available, acquiring a present reference scan before acquiring a sample scan. The method also includes comparing the present reference scan with the pre-existing reference spectrum to determine if there is one or more non-conformities therebetween and if there is/are one or more nonconformities, determining if the one or more non-conformities are resolvable or not. If the one or more non-conformities are resolvable; resolve each non-conformity in a determined manner and thereafter acquiring a scan of the sample, and if the non-conformities are not resolvable, then acquiring a new reference sample and thereafter acquiring a scan of the sample.

34 Claims, 7 Drawing Sheets

METHOD FOR REDUCING FREQUENCY OF TAKING BACKGROUND/REFERENCE SPECTRA IN FTIR OR FTIR-ATR SPECTROSCOPY AND HANDHELD MEASUREMENT DEVICE EMBODYING SAME

STATEMENT REGARDING FEDERALLY SPONSORED RESEARCH

This invention was made with government support under a contract with Naval Explosive Ordnance Disposal Technology Division (NAVEODTECHDIV), Task Order TI 69 and contract number N00174-13-C-0032. The government has certain rights in the invention.

FIELD OF INVENTION

The present invention relates to optical measurement and identification of samples and more particularly to methods for optical measurement that reduce frequency of taking background spectra, more specifically when using FTIR spectroscopy or FTIR-ATR spectroscopy techniques as well as measurement devices or apparatuses embodying such spectroscopic techniques.

BACKGROUND OF THE INVENTION

Many applications exist for methods to measure and identify unknown materials or substances as well as for portable measurement devices embodying such methods. Such applications include, for example, field identification of unknown substances by law enforcement, hazardous materials personnel, fire personnel and security personnel, as well as detection of prohibited substances at airports and in other secure and/or public locations, and identification of pharmaceutical agents, industrial chemicals, explosives, energetic materials, and other agents. Such field identification situations can include those where it is desirable to obtain such identification information under time critical situations. Also, to be useful in a variety of situations, it is advantageous for the portable measurement devices to have a handheld form factor and to rapidly provide accurate results.

In certain embodiments, the measurement devices and methods provide for contact between a sample of interest and the measurement device via a prism that is, for example, positioned in a protrusion of the measurement device's enclosure. The prism, which can be formed from a material such as diamond or Zinc Selenide, operates by ensuring that non-absorbed incident radiation is directed to a detector after undergoing total internal reflection within the prism. As a result, reflected radiation is coupled with high efficiency to the detector, ensuring sensitive operation of the measurement devices.

Samples of interest can be identified based on the reflected radiation that is measured by the detector. The reflected radiation can be used to derive infrared absorption information (e.g., absorption spectrum) corresponding to the sample, and the sample can be identified by comparing the infrared absorption information to reference information that is stored in the measurement device. In addition to the identity of the sample, the measurement device can provide one or more metrics (e.g., numerical results) that indicate how closely an infrared absorption spectrum or information matches the reference information. Further, the measurement device can compare the identity of the sample of interest to a list of prohibited substances—also stored within the measurement device—to determine whether particular precautions should be taken in handling the substance, and whether additional actions by security personnel or the like, for example, are warranted. A wide variety of different samples can be interrogated, including for example solids, liquids, gels, powders, and various mixtures of two or more substances.

When measuring the infrared absorption spectrum of a sample of interest using a conventional technique; a background or reference spectrum without the presence of the sample is typically taken close in time to acquiring the spectral information for the sample. The spectral data for the background or reference spectrum is taken so as to minimize environmental and/or instrument effects on the absorption spectrum being acquired.

The process for acquiring a background or reference spectrum typically involves performing or acquiring N scans of spectral data. As illustration, the process for certain measurement devices involves taking about 8 scans to arrive at a background or reference spectrum with an acceptable signal to noise ratio. This is not limiting as about 64 scans can be taken to establish a background spectrum, such as when the measurement device is being used under laboratory conditions.

Using techniques well known in the art (e.g., Fourier transform), the acquired spectral data is processed and combined so as to yield a background or reference spectrum. This background or reference spectrum is then used in combination with a subsequently acquired spectrum for a sample of interest to determine the spectral output or spectrum that is associated with the sample. This process of establishing a background or reference spectrum every time a sample is to be analyzed, however, may not be beneficial in some applications, such as when time is of the essence in determining the absorption spectrum associated with the sample, this process increases the time required to determine the make-up of the specific sample being analyzed.

One specific analysis technique that is used is generally referred to as Fourier Transform Infrared (FTIR) Spectroscopy which obtains infrared spectrum of absorption, emission or Raman scattering of a solid, liquid or gas. In this process a Fourier transform (a mathematical process) is used to convert the raw data into the actual spectrum. In use, an FTIR spectrometer simultaneously collects spectral data in a wide spectral range.

In FTIR spectroscopy, rather than shining a monochromatic beam of IR light at the sample, a beam containing many frequencies of infrared light shines on the sample, and one measures how much of that broadband beam is being absorbed (e.g., absorbed by the sample). Next, the beam is modified to contain a different combination of frequencies, giving a second data point. This process can be repeated as many times as desired. Afterwards, a computer deconvolves the acquired spectral data to infer what the absorption is at each wavelength. In other words, the computer (e.g., digital processor) processes the data so to yield a spectrum representative of the sample of interest.

The beam described above is generated by starting with a broadband light source—one containing the full spectrum of wavelengths (e.g., IR wavelengths) to be measured. The light shines into a Michelson interferometer—a certain configuration of mirrors, one of which is moved by a motor. As this mirror moves, each wavelength of light in the beam is periodically blocked, transmitted, blocked, transmitted, by the interferometer, due to wave interference. In this way, different wavelengths are modulated at different rates, so that at each moment, the beam coming out of the interferometer has a different spectral output.

Each such movement of the mirror generally corresponds to a scan and is generally considered the process of acquiring spectral data associated with one movement of the mirror. As indicated above, the absorption spectrum associated with the sample or the background results from a computer or other digital processing device/apparatus, taking all the acquired spectral data and processing it so as to infer what the absorption is at each wavelength.

There is found in U.S. Pat. No. 8,248,588 (owned by the assignee of the present invention), an apparatus that includes: (a) an enclosure including an aperture; (b) a prism mounted in the enclosure so that a surface of the prism is exposed through the aperture; (c) an optical assembly contained within the enclosure, the optical assembly including a radiation source and a radiation detector, the source being configured to direct radiation towards the prism and the detector being configured to detect radiation from the source reflected from the exposed surface of the prism; and (d) an electronic processor (e.g., digital processor) contained within the enclosure, the electronic processor being in communication with the detector. This apparatus can be configured so that, during operation, the electronic processor determines information about a sample placed in contact with the exposed surface of the prism based on radiation reflected from the exposed prism surface while it is in contact with the sample. Such an apparatus also routinely performs a process that yields a background or reference spectrum from N scans (e.g., 8 scans) as described herein, which process is undertaken close in time to the taking of the sample spectrum.

It thus would be desirable to provide new methods, devices and/or apparatuses that would be capable of reducing the frequency of taking background or reference spectra such as when using FTIR spectroscopy or FTIR-ATR spectroscopy. It would be particularly desirable to provide such a device and method that could be used as a portable chemical identification analyzer in the hot zone of an emergency response while not requiring the background or reference spectrum to be taken close in time to the taking of the sample spectrum. It also would be particularly desirable to perform checks prior to acquisition of the sample spectra which can be used to assess the ATR interface when using FTIR-ATR spectroscopy techniques, as well as compensating for changing conditions whenever possible.

SUMMARY OF THE INVENTION

In its broadest aspects, the present invention features a device(s), apparatus(s), system(s) and/or method(s) relating to any of a number of spectroscopic techniques. More particularly, there are featured a device(s), apparatus(s), system (s) and/or method(s) relating to FTIR spectroscopy or FTIR-ATR spectroscopy. Even more particularly, there is featured a method for reducing frequency of taking background or reference spectra when using FTIR spectroscopy or FTIR-ATR spectroscopy. In more particular aspects, such a method either (a) undertakes a process for determining the acceptability of a pre-existing reference spectrum before acquiring one or more scans of the sample or (b) undertakes a similar process for determining the acceptability of a pre-existing reference spectrum after first acquiring the one or more scans of the sample. As described further herein, either process for determining the acceptability of the pre-existing reference spectrum also includes resolving any spectral non-conformities with the pre-existing reference spectrum identified during such a process as herein further described. In the discussion herein reference to determining the acceptability of a pre-existing reference spectrum shall be understood to include determining the acceptability of a pre-existing reference spectrum that has been modified (i.e., modified pre-existing spectrum or modified reference spectrum) using the methodology of the present invention.

In more particular aspects, the present invention features a method for reducing frequency of taking background or reference spectra when using FTIR spectroscopy or FTIR-ATR spectroscopy. More particularly, such a method either (a) undertakes a process for determining the acceptability of a pre-existing reference spectrum before acquiring one or more scans of the sample or (b) undertakes a process in which the one or more scans of the sample are acquired first and then continues with performing a similar process for determining the acceptability of a pre-existing reference spectrum. As described further herein, either process for determining the acceptability of the pre-existing reference spectrum also includes resolving any spectral non-conformities with the pre-existing reference spectrum identified during such a process.

In this regard it should be understood that the terms "resolve, resolvable, resolving and the like" are used herein to generally describe or cover whatever means, algorithm, calculation, calibration information, graphical relationship, data or the like that can be used (alone or in combination) to correct, compensate for or otherwise address an identified non-conformity using the methodology of the present invention. Therefore, the use of such a term in combination with another term or phrase such as for example, compensating or correcting, shall not be considered as limiting the term resolve or the like.

In a more particular aspects, the present invention features a method for reducing frequency of taking background spectra when using one of FTIR spectroscopy or FTIR-ATR spectroscopy techniques, such a method includes the steps of determining if there is a pre-existing reference spectrum available; acquiring one or more scans of a sample of interest; and determining one of acceptability of the pre-existing reference spectrum or a modified pre-existing reference spectrum either (a) before acquiring the one or more scans of the sample or (b) after acquiring the one or more scans of the sample.

Such determining the acceptability of the pre-existing reference spectrum also includes acquiring a present reference scan; and comparing the present reference scan and the pre-existing reference spectrum to determine if there are any non-conformities there between. If one or more non-conformities are found between the present scan and the pre-existing reference spectrum, such a method includes determining if the one or more non-conformities are resolvable or not. If the one or more non-conformities are resolvable; then resolving each non-conformity in a manner determined to resolve the one or more non-conformities; and if the one or more non-conformities are not resolvable, then acquiring a new reference spectrum using any of a number of techniques as are known to those skilled in the art.

In further embodiments, such resolving further includes evaluating each non-conformity so as to determine if any of the non-conformities corresponds to a simple spectral artifact and not taking any action to correct for such simple spectral artifacts.

In yet further embodiments, such a method further includes storing one or more spectral shapes that are associated with one or more given spectral effects; and such resolving further includes comparing the one or more stored spectral shapes with the identified one or more non-conformities to determine a relationship between a given stored spectral shape and a particular non-conformity. If a relationship is determined or found, such resolving further includes using the stored spectral shape to determine a corrective action to resolve the non-conformity.

In yet further embodiments, such a method further includes storing other spectral information (e.g., algorithm, calculation, calibration information, graphical relationship, data or the like that can be used —alone or in combination- to correct, compensate for or otherwise address an identified non-conformity) and such resolving further includes evaluating each non-conformity with the other spectral information to determine if the other information relates to the non-conformity and the resolution of the non-conformity. If it is determined that the other information relates to the non-conformity, then such resolving also includes applying a corrective action related to the other information to resolve the non-conformity.

In yet further embodiments, such determining if the non-conformities are resolvable includes comparing spectrums for each of the present reference scan and the pre-existing reference spectrum to identify the spectral region(s) exhibiting a non-conformity; comparing each identified non-conformity with saved spectral information to determine if the non-conformity is one of environment related, instrument related or spectral related; and determining if the non-conformity with the pre-existing reference spectrum is resolvable by adjusting the pre-existing spectrum based on the saved information and the present reference scan. If such determining determines that the pre-existing reference spectrum is resolvable, then the process proceeds with adjusting the pre-existing reference spectrum.

In yet further embodiments, the spectroscopy technique embodies an ATR interface and wherein said resolving includes evaluating the one or more non-conformities to determine if one or more non-conformities are indicators of a dirty ATR interface. If the ATR interface is determined to be a dirty interface, the process continues with providing an indication to clean the interface.

Such an indication for cleaning can be in any form known in the art including but not limited to, for example, a visual or auditory signal or message, an automatic signal to a device or the like to initiate the cleaning process or a combination thereof. In more particular embodiments, such a visual or auditory signal can be provided to the user to allow the user to manually perform the cleaning process or to start an automated cleaning process. In addition, after cleaning of the interface, such a process includes repeating the steps of acquiring, comparing and determining to determine if the ATR interface is clean.

In yet further embodiments, after cleaning the interface and repeating said determining if one or more non-conformities are indicators of a dirty ATR interface, the process includes determining if this is the first time such a determination is being made. If it is determined that this is not the first time such a determination is being made, then causing the process to proceed to acquiring a new reference sample.

In yet further embodiments, before acquiring the one or more scans of the sample, such a method includes providing a message to a user that instructs the user to take the actions involved with acquiring the sample spectrum; and after acquiring the sample spectrum, analyzing the sample scan(s) in conjunction with one of the pre-existing reference spectrum or the modified pre-existing reference spectrum so as to yield a corrected sample spectrum. Also, after such analyzing is performed, the method includes providing results of such analyzing to the user. In more particular embodiments, such providing includes displaying the results to the user.

In yet more particular embodiments, before acquiring a present reference scan and after determining that a pre-existing reference spectrum is available; such a method includes determining if a predetermined amount of time has elapsed or not since the pre-existing reference spectrum was acquired; if a predetermined amount of time has elapsed then causing the process to proceed to acquiring a new reference spectrum and if a predetermined time has not elapsed then causing the process to proceed with acquiring a present scan and the process that follows for determining the acceptability of the pre-existing reference spectrum or the modified pre-existing reference spectrum.

According to a more particular aspect/embodiments of the present invention such a method for reducing frequency of taking background spectra when using one of FTIR spectroscopy or FTIR-ATR spectroscopy techniques either before or after acquiring the one or more sample scans, further includes an alternative mechanism that provides an additional check on the acceptability of a pre-existing reference spectrum or a modified reference spectrum based in part on the pre-existing reference spectrum. As also indicated herein, it also should be recognized that it is within the scope of the present invention for such a methodology to be embodied in an applications program.

In further aspects/embodiments, such a methodology further includes determining if a predetermined amount of time has elapsed or not since the pre-existing reference spectrum was acquired. In the case where a predetermined amount of time has elapsed, then the process is caused to proceed to acquiring a new reference spectrum and thereafter acquiring one or more scans of the sample. In other words, after a sufficient amount of time has elapsed it is presumed that the pre-existing reference spectrum has become stale and thus should not be used any further. On the other hand, if a predetermined time has not elapsed then the process proceeds to the step of acquiring a present reference scan.

In yet further aspects/embodiments, such a methodology further includes determining if a predetermined amount of time has elapsed or not since a check was made of the acceptability of the pre-existing reference spectrum or the modified pre-existing reference spectrum. In this example, the methodology is arranged so that it continues to perform sample scanning while using the pre-existing reference spectrum or modified reference spectrum that was first checked using such a methodology. In the case where a predetermined amount of time has elapsed, then the process is caused to re-check or again check the pre-existing reference spectrum or modified reference spectrum. Using this process the methodology determines if it is acceptable to continue using the reference spectrum it had been using or if a new reference spectrum should be acquired or if the reference spectrum that was being used should be modified or further modified. On the other hand, if the predetermined time has not elapsed then the process continues using the reference spectrum that was being used and also to continue with acquisition of one or more sample scans.

According to another aspect of the present invention in which the acceptability of a pre-existing reference spectrum is assessed or determined before acquiring one or more scans of the sample, such a method for reducing the frequency of taking background or reference spectra when using FTIR spectroscopy or FTIR-ATR spectroscopy includes determining if there is a pre-existing reference spectrum available and acquiring a present reference scan before acquiring a sample scan. It should be recognized, however, that such a method can be adapted to perform such a methodology after acquiring a sample scan as herein described. The method continues with comparing the present reference scan with the pre-existing reference spectrum to determine if the pre-existing reference spectrum is acceptable for further use. More particularly, the present reference scan and the pre-existing reference spectrum are compared to determine if, there are any (e.g., one or more) non-conformities between the two and to identify such non-conformities. If there are no non-conformities found between the present scan and the pre-existing reference spectrum, then the process continues with acquiring a sample scan for a sample of interest.

If on the other hand one or more non-conformities is/are found between the present scan and the pre-existing reference spectrum, then the process continues with determining if the identified non-conformity/non-conformities is/are resolvable or not. If resolvable, then the process updates the pre-existing reference spectrum (if required) in a manner that is determined to resolve the one or more non-conformities, and the process continues with acquiring the sample scan.

In this regard it should be understood that the terms "resolve, resolvable, resolving and the like" are used herein to generally describe or cover whatever means, algorithm, calculation, calibration information, graphical relationship, data or the like that can be used (alone or in combination) to correct, compensate for or otherwise address an identified non-conformity using the methodology of the present invention. Therefore, the use of such a term in combination with another term or phrase such as for example, compensating or correcting, shall not be considered as limiting the term resolve or the like. In yet further embodiments, such a method continues with analyzing each identified non-conformity to determine if the non-conformity corresponds to a simple spectral anomaly (e.g., water absorption within a known absorption wavelength range). If it is determined that a non-conformity is a simple spectral anomaly, the process continues with eliminating or ignoring the presence of such simple spectral artifacts. In other words, the pre-existing reference spectrum is not corrected to account for the effect of the simple spectral anomaly.

In yet further embodiments, such a method further includes fitting spectral shapes to the non-conformity to determine if the non-conformity can be adjusted, eliminated or otherwise dealt with using such a spectral shape and information associated with the spectral shape. If it is determined that a non-conformity corresponds to such a spectral shape or is a simple spectral anomaly, the process continues with compensating for or resolving each non-conformity based on the fitted spectral shape(s), the related information and the pre-existing reference spectrum.

In further embodiments, other information such as algorithms, calculations, calibration information and the like is made available and the non-conformity is evaluated using such other information. From such an evaluation, it is determined how to resolve or compensate for one or more non-conformities using such information. Thereafter, the pre-existing reference spectrum can be adjusted or compensated for using the applicable other information.

In yet further embodiments, a resultant reference spectrum is created using such information resolving or compensating for a non-conformity. Such a resultant reference spectrum is preferably saved and replaces the pre-existing reference spectrum for future sample scanning purposes (e.g., becomes a modified pre-existing reference spectrum or modified reference spectrum).

In further embodiments, such as when using FTIR-ATR spectroscopy techniques, in determining if the non-conformities are resolvable, the process also continues with determining if the ATR interface is clean or not. If it is determined that one or more identified non-conformities suggest that the ATR interface might be dirty, then the process continues with causing the cleaning of the ATR interface. As indicated herein, in more particular aspects/embodiments, if the ATR interface is determined to be a dirty interface, the process continues with providing an indication to clean the interface. Such an indication for cleaning can be in any form known in the art including but not limited to, for example, a visual or auditory signal or message, an automatic signal to a device or the like to initiate the cleaning process or a combination thereof. In more particular embodiments, such a visual or auditory signal can be provided to the user to allow the user to manually perform the cleaning process or to start an automated cleaning process.

According to a more particular aspect/embodiments of the present invention such a method for reducing frequency of taking background spectra when using one of FTIR spectroscopy or FTIR-ATR spectroscopy techniques before acquiring the one or more sample scans, further includes an alternative mechanism that provides an additional check on the acceptability of a pre-existing reference spectrum or a modified reference spectrum that is based in part on the pre-existing reference spectrum. As also indicated herein, it also should be recognized that it is within the scope of the present invention for such a methodology to be embodied in an applications program.

In further aspects/embodiments, such a methodology further includes determining if a predetermined amount of time has elapsed or not since the pre-existing reference spectrum was acquired. In the case where the predetermined amount of time has elapsed, then the process is caused to proceed to acquiring a new reference spectrum and thereafter acquiring one or more scans of the sample. In other words, after a sufficient amount of time has elapsed it is presumed that the pre-existing reference spectrum has become stale and thus should not be used any further. On the other hand, if a predetermined time has not elapsed the causing the process proceeds to the step of acquiring a present reference scan before acquiring a sample spectrum.

In yet further aspects/embodiments, such a methodology further includes determining if a predetermined amount of time has elapsed or not since a check was made of the acceptability of the pre-existing reference spectrum or the modified pre-existing reference spectrum. In this example, the methodology is arranged so that it continues to perform sample scanning while using the pre-existing reference spectrum or modified reference spectrum that was first checked using such a methodology. In the case where a predetermined amount of time has elapsed, then the process is caused to re-check or again check the pre-existing reference spectrum or modified reference spectrum. Using this process the methodology determines if it is acceptable to continue using the reference spectrum it had been using or if a new reference spectrum should be acquired or if the reference spectrum that was being used should be modified or further modified. On the other hand, if the predetermined time has not elapsed then the process continues using the reference spectrum that was being used and also continues with acquisition of one or more sample scans.

According to another aspect of the present invention, there is featured an applications program for execution on a logic circuit including a digital processor or microprocessor. According to yet another aspect of the present invention, there is featured a non-transitory computer medium on which is stored an applications program for execution on a logic circuit including a digital processor or microprocessor. According to still yet another aspect of the present invention, there is featured a computer system including a logic circuit such as digital processor and an applications program for execution on the logic circuit. In embodiments, such a computer system further includes a storage medium operable coupled to the logic circuit, where the applications program is stored on the storage medium.

As also indicated herein, such applications programs of the present invention are configurable such that they can either (a) undertake a process for determining the acceptability of a pre-existing reference spectrum or a modified pre-existing spectrum before acquiring one or more scans of the sample or (b) undertake a similar process for determining the acceptability of a pre-existing reference spectrum or modified reference spectrum after first acquiring the one or more scans of the sample. As described further herein, such applications programs include a process for determining the acceptability of the pre-existing reference spectrum or modified reference spectrum which also includes identifying and resolving any spectral non-conformities with the pre-existing reference spectrum during such a process as further described herein. Reference also shall be made to the foregoing discussions concerning the above-described methodologies of the present invention for further details of the method steps referred to in the following discussion of the applications programs according to these aspects of the present invention unless otherwise discussed below. Also, reference shall be made to the forgoing discussion regarding the terms "resolve, resolvable, resolving and the like" which also applies here.

In one particular aspect, such an applications program includes instructions, criteria and code segments for performing a methodology including the steps of the present invention. More specifically such a method includes processes for reducing frequency of taking background or reference spectra when using FTIR spectroscopy or FTIR-ATR spectroscopy and even more particularly, either (a) undertakes a process for determining the acceptability of a pre-existing reference spectrum before acquiring one or more scans of the sample or (b) undertakes a process in which the one or more scans of the sample are acquired first and then performs a similar process for determining the acceptability of a pre-existing reference spectrum or modified reference spectrum. As described further herein, either process for determining the acceptability of the pre-existing reference spectrum or modified reference spectrum also includes resolving any spectral non-conformities with the pre-existing reference spectrum or modified reference spectrum identified during such a process.

In more particular aspects, said instructions, criteria and code segments are such as to further perform the method step(s) of determining if there is a pre-existing reference spectrum available; acquiring one or more scans of a sample of interest; and determining one of acceptability of the pre-existing reference spectrum or of a modified pre-existing reference spectrum either (a) before acquiring the one or more scans of the sample or (b) after acquiring the one or more scans of the sample.

Such determining the acceptability of the pre-existing reference spectrum or of the modified pre-existing reference spectrum also includes instructions, criteria and code segments for acquiring a present reference scan; and comparing the present reference scan and the pre-existing reference spectrum to determine if there are any non-conformities there between. If one or more non-conformities are found between the present scan and the pre-existing reference spectrum, such instructions, criteria and code segments further includes determining if the one or more non-conformities are resolvable or not. If the one or more non-conformities are resolvable; resolving each non-conformity in a manner determined to resolve the one or more non-conformities; and if the one or more non-conformities are not resolvable, then acquiring a new reference spectrum using any of a number of techniques as are known to those skilled in the art.

In embodiments of the present invention, such resolving further includes instructions, criteria and code segments for evaluating each non-conformity so as to determine if any of the non-conformities correspond to a simple spectral artifact and for those non-conformities categorized as being a simple spectral artifact taking no action to compensate for such simple spectral artifacts.

In yet further embodiments, said instructions, criteria and code segments are such as to further perform the method step(s) of storing one or more spectral shapes that are associated with one or more given spectral effects; and such resolving further includes instructions, criteria and code segments for comparing the one or more stored spectral shapes with the identified one or more non-conformities to determine a relationship between a given stored spectral shape and a particular non-conformity. If a relationship is determined or found, such resolving further includes instructions, criteria and code segments for using the stored spectral shape to determine a corrective action to resolve the non-conformity.

In yet further embodiments, said instructions, criteria and code segments are such as to further perform the method step(s) of storing other spectral information (e.g., algorithm, calculation, calibration information, graphical relationship, data or the like that can be used —alone or in combination- to correct, compensate for or otherwise address an identified non-conformity) and such resolving further includes instructions, criteria and code segments for evaluating each non-conformity with the other spectral information to determine if the other information relates to the non-conformity and the resolution of the non-conformity. If it is determined that the other information relates to the non-conformity, then such resolving also includes instructions, criteria and code segments for applying a corrective action related to the other information to resolve the non-conformity.

In yet further embodiments, such determining if the non-conformities are resolvable includes instructions, criteria and code segments for comparing spectrums for each of the present reference scan and the pre-existing reference spectrum to identify the spectral region(s) exhibiting a non-conformity; comparing each identified non-conformity with saved spectral information to determine if the non-conformity is one of environment related, instrument related or spectral related; and determining if the non-conformity with the pre-existing reference spectrum is resolvable by adjusting the pre-existing spectrum based on the saved information and the present reference scan. If such determining determines that the pre-existing reference spectrum is resolvable, then the instructions, criteria and code segments are such that the process proceeds with adjusting the pre-existing reference spectrum.

In yet further embodiments, the spectroscopy technique embodies an ATR interface and wherein said resolving includes instructions, criteria and code segments for evaluating the one or more non-conformities to determine if the one or more non-conformities are indicators of a dirty ATR interface. If the ATR interface is determined to be a dirty interface, then the instructions, criteria and code segments are such that the process continues with providing an indication to clean the interface.

Such an indication for cleaning can be in any form known in the art including but not limited to, for example, a visual or auditory signal or message, an automatic signal to a device or the like to initiate the cleaning process or a combination thereof. In more particular embodiments, such a visual or auditory signal can be provided to the user to allow the user to manually perform a cleaning process or to start an automated cleaning process. In addition, after cleaning of the interface, the process includes repeating the steps of acquiring, comparing and determining to determine if the ATR interface is clean.

In yet further embodiments, after cleaning the interface and repeating said determining if one or more non-conformities are indicators of a dirty ATR interface, the instructions, criteria and code segments are such that the process proceeds with determining if this is the first time such a determination of a dirty interface is being made. If it is determined that this is not the first time, then the instructions, criteria and code segments also are such as to cause the process to proceed to acquiring a new reference sample.

In yet further embodiments, before acquiring the one or more scans of the sample, said instructions, criteria and code segments are such as to perform the step(s) of providing a message to a user that instructs the user to take the actions involved with acquiring the sample spectrum; and after acquiring the sample spectrum, analyzing the sample scan(s) in conjunction with one of the pre-existing reference spectrum or the modified pre-existing reference spectrum so as to yield a corrected sample spectrum. Also, after such analyzing is performed, said instructions, criteria and code segments are such as to perform the step(s) of providing results of such analyzing to the user. In more particular embodiments, such providing includes displaying the results to the user.

In yet more particular embodiments, before acquiring a present reference scan and after determining that a pre-existing reference spectrum is available; said instructions, criteria and code segments are such as to perform the step(s) of determining if a predetermined amount of time has elapsed or not since the pre-existing reference spectrum was acquired; if a predetermined amount of time has elapsed then causing the process to proceed to acquiring a new reference spectrum and if a predetermined time has not elapsed then causing the process to proceed with acquiring a present scan and the process that follows for determining the acceptability of the pre-existing reference spectrum or the modified pre-existing reference spectrum.

In yet further aspects/embodiments, said instructions, criteria and code segments are such as to perform the step(s) of determining if a predetermined amount of time has elapsed or not since a check was made of the acceptability of the pre-existing reference spectrum or the modified pre-existing reference spectrum. In this example, the methodology is arranged so that it continues to perform sample scanning while using the pre-existing reference spectrum or modified reference spectrum that was first checked using such a methodology. In the case where a predetermined amount of time has elapsed, then the process is caused to re-check or again check the pre-existing reference spectrum or modified reference spectrum. Using this process the methodology determines if it is acceptable to continue using the reference spectrum it had been using or if a new reference spectrum should be acquired or if the reference spectrum that was being used should be modified or further modified. On the other hand, if the predetermined time has not elapsed then the process continues using the reference spectrum that was being used and also to continue with acquisition of one or more sample scans.

According to another particular aspect, there is featured another applications program that includes instructions, criteria and code segments for performing a methodology including the steps of the present invention. More particularly, such a methodology includes processes for reducing frequency of taking background or reference spectra when using FTIR spectroscopy or FTIR-ATR spectroscopy and even more particularly, such processes include determining the acceptability of a pre-existing reference spectrum or modified pre-existing reference spectrum before acquiring one or more scans of the sample. As described further herein, such a process for determining the acceptability of the pre-existing reference spectrum or modified reference spectrum also includes resolving any spectral non-conformities with the pre-existing reference spectrum or modified reference spectrum identified during such a process.

Such an applications program according to these aspects of the present invention includes instructions, criteria and code segments for performing a methodology including the steps of determining if there is a pre-existing reference spectrum available and, if such a reference spectrum is available, acquiring a present reference scan before acquiring a sample spectrum and comparing the present reference scan and the pre-existing reference spectrum to determine if there are any non-conformities there between. If one or more non-conformities are found between the present scan and the pre-existing reference spectrum, such instructions, criteria and code segments further include determining if the one or more non-conformities are resolvable or not. If the one or more non-conformities are resolvable; such instructions, criteria and code segments include resolving each non-conformity in a determined manner and thereafter acquiring a spectrum of the sample; and if the one or more non-conformities are not resolvable, then such instructions, criteria and code segments include acquiring a new reference spectrum and thereafter acquiring a spectrum of the sample (e.g., from one or more scans of the sample).

In embodiments of the present invention, such resolving further includes instructions, criteria and code segments for evaluating each non-conformity so as to determine if any of the non-conformities corresponds to a simple spectral artifact and for those non-conformities categorized as being a simple spectral artifact taking no action to compensate for such simple spectral artifacts.

In further embodiments, said instructions, criteria and code segments are such as to further perform the method step(s) of storing one or more spectral shapes that are associated with one or more given spectral effects. In addition, such resolving further includes instructions, criteria and code segments for comparing the one or more stored spectral shapes with the identified one or more non-conformities to determine a relationship between a given stored spectral shape and a particular non-conformity; and if a relationship is determined, using the stored spectral shape to determine a corrective action to resolve the non-conformity.

In yet further embodiments, said determining if the non-conformities are resolvable further includes instructions, criteria and code segments for: comparing spectrums for each of a present scan and the pre-existing reference spectrum to identify the spectral region(s) exhibiting a non-conformity; comparing each identified non-conformity with saved spectral information to determine if the non-conformity is one of environment related, instrument related or spectral related; and determining if the non-conformity with the pre-existing reference spectrum is resolvable by adjusting the pre-existing spectrum based on the saved information and the present reference scan. If said determining determines that the pre-existing reference spectrum is adjustable, adjusting the pre-existing reference spectrum and then proceed with acquiring a spectrum of the sample.

In yet further embodiments, said instructions, criteria and code segments are such as to further perform the method steps of storing other spectral information (such as that described herein). Additionally, such resolving further includes instructions, criteria and code segments for evaluating each non-conformity with the other spectral information to determine if the other information relates to the non-conformity and the resolution of the non-conformity and if it is determined that the other information relates, then applying a corrective action related to the other information.

In the case where such an applications program is used in connection with an FTIR-ATR spectroscopy technique and where the spectroscopy technique embodies an ATR interface, then such resolving further includes instructions, criteria and code segments for evaluating the one or more non-conformities to determine if the one or more non-conformities are indicators of a dirty ATR interface. If it is determined that the ATR interface is dirty or not clean, then the instructions, criteria and code segments further include providing an indication to a user to clean the interface.

Such an indication for cleaning can be in any form known in the art including but not limited to, for example, a visual or auditory signal or message, an automatic signal to a device or the like to initiate the cleaning process or a combination thereof. In more particular embodiments, such a visual or auditory signal can be provided to the user to allow the user to manually perform a cleaning process or to start an automated cleaning process. In addition, after cleaning of the interface, the process includes repeating the steps of acquiring, comparing and determining to determine if the ATR interface is clean.

After cleaning the interface, the instructions, criteria and code segments are such so that said acquiring, comparing and determining to determine if the "cleaned" ATR interface is clean or not, are repeated. In more particular embodiments, after cleaning the interface and repeating said determining if one or more non-conformities are indicators of a dirty ATR interface, the instructions, criteria and code segments further include determining if this is the first time such a determination is being made, and if it is determined that this is not the first time, then the instructions, criteria and code segments cause the process to proceed with acquiring a new reference sample and thereafter acquiring a spectrum of the sample if it is again determined that the interface is dirty.

In yet further embodiments, the said instructions, criteria and code segments are such as to further perform the method step(s) of: before acquiring the sample spectrum, providing a message to a user that instructs the user to take the actions to acquire the sample spectrum; and after acquiring the sample spectrum, analyzing the sample scan(s) or sample spectrum in conjunction with one of the pre-existing background reference spectrum or a modified pre-existing reference spectrum so as to yield a corrected sample spectrum. In addition, such instructions, criteria and code segments are such as to further perform the method step(s) of after said analyzing is performed, providing results of such analyzing to the user. Also, such providing further includes instructions, criteria and code segments for displaying the results to the user.

According to a more particular aspect/embodiment of the present invention such an applications program includes instruction, criteria, and code segments so as to provide an alternative mechanism that provides an additional check on the acceptability of the pre-existing reference spectrum or the modified reference spectrum. In further aspects/embodiments, such instructions, criteria and code segments are such as to perform the method step(s) of determining if a predetermined amount of time has elapsed or not since the pre-existing reference spectrum was acquired. In the case where a predetermined amount of time has elapsed, then the instructions, criteria and code segments are such as to cause the process to proceed to acquiring a new reference spectrum and thereafter acquiring one or more scans of the sample. In other words, after a sufficient amount of time has elapsed it is presumed that the pre-existing reference spectrum or modified spectrum has become stale and thus should not be used any further. On the other hand, if a predetermined time has not elapsed then the instructions, criteria and code segments are such as to cause the process to proceed with the step of acquiring a present reference scan before acquiring a sample spectrum.

In yet further aspects/embodiments, such instructions, criteria and code segments are such as to also perform the method step(s) of determining if a predetermined amount of time has elapsed or not since a check was made of the acceptability of the pre-existing reference spectrum or the modified pre-existing reference spectrum. For example, the methodology including the instructions, criteria and code segments of a related applications program is arranged so that it continues to perform sample scanning while using the pre-existing reference spectrum or modified reference spectrum that was first checked using such a methodology. In the case where a predetermined amount of time has elapsed, then the instructions, criteria and code segments are such as to cause the process to re-check or again check the pre-existing reference spectrum or modified reference spectrum. The instructions, criteria and code segments of such a process are such as to determine if it is acceptable to continue using the reference spectrum it had been using or if a new reference spectrum should be acquired or if the reference spectrum that was being used should be modified or further modified. On the other hand, the instructions, criteria and code segments are such that if the predetermined time has not elapsed then the process continues using the reference spectrum that was being used and also to continue with acquisition of one or more sample scans.

According to yet another aspect of the present invention, there is featured a measurement apparatus for us in one of FTIR spectroscopy and FTIR-ATR spectroscopy of a sample. Reference shall be made to the foregoing discussion concerning the methodology of the present invention and the applications program of the present invention for details of the method steps referred to in the following discussion as to the applications program according to these aspects of the present invention unless otherwise discussed below. As also indicated herein, the methods and applications programs of the present invention can be arranged or configured so that certain processes of each can be performed prior to performing sample scanning or after performing sample scanning. More specifically, the processes involved with determining the acceptability of a pre-existing reference spectrum or a modified pre-existing reference spectrum can be performed prior to performing sample scanning or after performing sample scanning. Also reference shall be made to the forgoing discussion regarding the terms "resolve, resolvable, resolving and the like" which also applies here.

In yet further aspects/embodiments, such a measurement apparatus includes a means for irradiating the sample; a detection device that is configured and arranged to detect radiation emanating from the sample and providing an output of the detected radiation; a processing device including a digital processor or microprocessor, which is operably coupled to the detection device for controlling operation of the measurement apparatus including the irradiating means and the detection device and processing the detection device outputs; and an applications program for execution on the processing device.

In more specific embodiments, such a means for irradiating the sample comprises any of a number of means known to those skilled in the art which can irradiate the sample with a broad band spectrum of radiation, for example a broad band of IR radiation. Such a means can include a single emitter as well as a plurality of emitters. In the case of a plurality of emitters, such a measurement apparatus, for example the processing device, can selectively control operation of the individual emitters so as to provide individual broad bands of radiation that can be composed of different frequencies of radiation.

Such an applications program includes instructions, criteria and code segments for executing or performing any methodology according to the present invention. More specifically and according to one particular aspect of the present invention, such a method includes processes for reducing frequency of taking background or reference spectra when using FTIR spectroscopy or FTIR-ATR spectroscopy and even more particularly, either (a) undertakes a process for determining the acceptability of a pre-existing reference spectrum or modified pre-existing reference spectrum before acquiring one or more scans of the sample or (b) undertakes a process in which the one or more scans of the sample are acquired first and then performs a similar process for determining the acceptability of a pre-existing reference spectrum or modified reference spectrum. As described further herein, either process for determining the acceptability of the pre-existing reference spectrum or modified reference spectrum also includes resolving any spectral non-conformities with the pre-existing reference spectrum or modified reference spectrum identified during such a process.

In more particular aspects/embodiments, the instructions, criteria and code segments are such as to further perform the method step(s) of determining if there is a pre-existing reference spectrum available; acquiring one or more scans of a sample of interest; and determining the acceptability of the pre-existing reference spectrum or of a modified pre-existing reference spectrum either (a) before acquiring the one or more scans of the sample or (b) after acquiring the one or more scans of the sample.

Such determining the acceptability of the pre-existing reference spectrum or of the modified pre-existing reference spectrum also includes instructions, criteria and code segments for acquiring a present reference scan; and comparing the present reference scan and the pre-existing reference spectrum to determine if there are any non-conformities there between. If one or more non-conformities are found between the present scan and the pre-existing reference spectrum, such instructions, criteria and code segments further includes determining if the one or more non-conformities are resolvable or not. If the one or more non-conformities are resolvable; such instructions, criteria and code segments further includes resolving each non-conformity in a manner determined to resolve the one or more non-conformities; and if the one or more non-conformities are not resolvable, then such instructions, criteria and code segments further includes acquiring a new reference spectrum using any of a number of techniques as are known to those skilled in the art.

In embodiments of the present invention, such resolving further includes instructions, criteria and code segments for evaluating each non-conformity so as to determine if any of the non-conformities corresponds to a simple spectral artifact and for those non-conformities categorized as being a simple spectral artifact taking no action to compensate for such simple spectral artifacts.

In yet further embodiments, said instructions, criteria and code segments are such as to further perform the method step(s) of storing one or more spectral shapes that are associated with one or more given spectral effects; and such resolving further includes instructions, criteria and code segments for comparing the one or more stored spectral shapes with the identified one or more non-conformities to determine a relationship between a given stored spectral shape and a particular non-conformity. If a relationship is determined or found, such resolving further includes instructions, criteria and code segments for using the stored spectral shape to determine a corrective action to resolve the non-conformity.

In yet further embodiments, said instructions, criteria and code segments are such as to further perform the method step(s) of storing other spectral information (e.g., algorithm, calculation, calibration information, graphical relationship, data or the like that can be used —alone or in combination- to correct, compensate for or otherwise address an identified non-conformity) and such resolving further includes instructions, criteria and code segments for evaluating each non-conformity with the other spectral information to determine if the other information relates to the non-conformity and the resolution of the non-conformity. If it is determined that the other information relates to the non-conformity, then such resolving also includes instructions, criteria and code segments for applying a corrective action related to the other information to resolve the non-conformity.

In yet further embodiments, such determining if the non-conformities are resolvable includes instructions, criteria and code segments for comparing spectrums for each of the present reference scan and the pre-existing reference spectrum to identify the spectral region(s) exhibiting a non-conformity; comparing each identified non-conformity with saved spectral information to determine if the non-conformity is one of environment related, instrument related or spectral related; and determining if the non-conformity with the pre-existing reference spectrum is resolvable by adjusting the pre-existing spectrum based on the saved information and the present reference scan. If such determining determines that the pre-existing reference spectrum is resolvable, then the instructions, criteria and code segments are such that the process proceeds with adjusting the pre-existing reference spectrum.

In yet further embodiments, the spectroscopy technique embodies an ATR interface and wherein said resolving includes instructions, criteria and code segments for evaluating the one or more non-conformities to determine if one or more of the non-conformities are indicators of a dirty ATR interface. If the ATR interface is determined to be a dirty interface, then the instructions, criteria and code segments are such that the process continues with providing an indication to clean the interface.

Such an indication for cleaning can be in any form known in the art including but not limited to, for example, a visual or auditory signal, a message, and an automatic signal to a device or the like to initiate the cleaning process or a combination thereof. In more particular embodiments, such a visual or auditory signal can be provided to the user to allow the user to manually perform a cleaning process or to start an automated cleaning process. In addition, after cleaning of the interface, said resolving includes instructions, criteria and code segments for repeating the steps of acquiring, comparing and determining to determine if the ATR interface is clean.

In yet further embodiments, after cleaning the interface and repeating said determining if one or more non-conformities are indicators of a dirty ATR interface, the instructions, criteria and code segments are such that the process proceeds with determining if this is the first time such a determination is being made. If it is determined that this is not the first time, then the instructions, criteria and code segments also are such as to cause the process to proceed to acquiring a new reference sample.

In yet further embodiments, before acquiring the one or more scans of the sample, such instructions, criteria and code segments are such as to perform the step(s) of providing a message to a user that instructs the user to take the actions involved with acquiring the sample spectrum; and after acquiring the sample spectrum, analyzing the sample scan(s) in conjunction with one of the pre-existing reference spectrum or the modified pre-existing reference spectrum so as to yield a corrected sample spectrum. Also, after such analyzing is performed, such instructions, criteria and code segments are such as to perform the step(s) of providing results of such analyzing to the user. In more particular embodiments, such providing includes displaying the results to the user.

In yet more particular embodiments, before acquiring a present reference scan and after determining that a pre-existing reference spectrum is available; such instructions, criteria and code segments are such as to perform the step(s) of determining if a predetermined amount of time has elapsed or not since the pre-existing reference spectrum was acquired; if a predetermined amount of time has elapsed then causing the process to proceed to acquiring a new reference spectrum and if a predetermined time has not elapsed then causing the process to proceed with acquiring a present scan and the process that follows for determining the acceptability of the pre-existing reference spectrum or the modified pre-existing reference spectrum.

In further aspects/embodiments, such instructions, criteria and code segments are such as to perform the step(s) of determining if a predetermined amount of time has elapsed or not since the pre-existing reference spectrum was acquired. In the case where a predetermined amount of time has elapsed, then the process is caused to proceed to acquiring a new reference spectrum and thereafter acquiring one or more scans of the sample. In other words, after a sufficient amount of time has elapsed it is presumed that the pre-existing reference spectrum has become stale and thus should not be used any further. On the other hand, if a predetermined time has not elapsed such instructions, criteria and code segments cause the process to proceed to the step of acquiring a present reference scan before acquiring a sample spectrum.

In yet more particular embodiments, before acquiring a present reference scan and after determining that a pre-existing reference spectrum is available; said instructions, criteria and code segments are such as to perform the step(s) of determining if a predetermined amount of time has elapsed or not since the pre-existing reference spectrum was acquired; if a predetermined amount of time has elapsed then causing the process to proceed to acquiring a new reference spectrum and if a predetermined time has not elapsed then causing the process to proceed with acquiring a present scan and the process that follows for determining the acceptability of the pre-existing reference spectrum or the modified pre-existing reference spectrum.

In yet further aspects/embodiments, such instructions, criteria and code segments are such as to perform the step(s) of determining if a predetermined amount of time has elapsed or not since a check was made of the acceptability of the pre-existing reference spectrum or the modified pre-existing reference spectrum. In this aspect/embodiment, the methodology is arranged so that it continues to perform sample scanning while using the pre-existing reference spectrum or modified reference spectrum that was first checked using such a methodology. In the case where a predetermined amount of time has elapsed, then the process is caused to re-check or again check the pre-existing reference spectrum or modified reference spectrum. Using this process the methodology determines if it is acceptable to continue using the reference spectrum it had been using or if a new reference spectrum should be acquired or if the reference spectrum that was being used should be modified or further modified. On the other hand, if the predetermined time has not elapsed then the process continues using the reference spectrum that was being used and also to continue with acquisition of one or more sample scans.

According to another particular aspect, there is featured another applications program that includes instructions, criteria and code segments for performing a methodology that includes processes for reducing frequency of taking background or reference spectra when using FTIR spectroscopy or FTIR-ATR spectroscopy and even more particularly, such processes include determining the acceptability of a pre-existing reference spectrum or modified pre-existing reference spectrum before acquiring one or more scans of the sample. As described further herein, such a process for determining the acceptability of the pre-existing reference spectrum or modified reference spectrum also includes resolving any spectral non-conformities with the pre-existing reference spectrum or modified reference spectrum identified during such a process.

Such an applications program including instructions, criteria and code segments for carrying out a methodology including the steps of: determining if there is a pre-existing reference spectrum available; if such a reference spectrum is available, acquiring a present reference scan before acquiring a sample spectrum; and comparing the present reference scan and the pre-existing reference spectrum to determine if there are any non-conformities there between. If one or more non-conformities are found between the present scan and the pre-existing reference spectrum, such instructions, criteria and code segments include determining if the one or more non-conformities are resolvable or not. If the one or more non-conformities are resolvable; such instructions, criteria and code segments include resolving each non-conformity in a determined manner and thereafter acquiring one or more scans of the sample; and if the one or more non-conformities are not resolvable, then acquiring a new reference sample and thereafter acquiring the one or more scans of the sample. See also discussions herein regarding the terms, resolve and the like as well as the discussion herein regarding pre-existing reference spectrum and modified pre-existing reference spectrum which also apply here.

In further embodiments, such resolving further includes instructions, criteria and code segments for evaluating each non-conformity so as to determine if any of the non-conformities corresponds to a simple spectral artifact and for those non-conformities categorized as being a simple spectral artifact taking no action to compensate for such simple spectral artifacts.

In yet further embodiments, the instructions, criteria and code segments are such as to further perform the method step(s) of storing one or more spectral shapes that are associated with one or more given spectral effects; and such resolving further includes instructions, criteria and code segments for comparing the one or more stored spectral shapes with the identified one or more non-conformities to determine a relationship between a given stored spectral shape and a particular non-conformity. If a relationship is determined, then such resolving further includes instructions, criteria and code segments for using the stored spectral shape to determine a corrective action to resolve the non-conformity.

In yet further embodiments, such determining if the non-conformities are resolvable further includes instructions, criteria and code segments for: comparing spectrums for each of a present scan and the pre-existing reference spectrum to identify the spectral region(s) exhibiting a non-conformity; comparing each identified non-conformity with saved spectral information to determine if the non-conformity is one of environment related, instrument related or spectral related; and determining if the non-conformity with the pre-existing reference spectrum is resolvable by adjusting the pre-existing spectrum based on the saved information and the present reference scan. If such determining determines that the pre-existing reference spectrum is adjustable, such instructions, criteria and code segments include adjusting the pre-existing reference spectrum and then proceed with acquiring the sample spectrum (e.g., from the one or more scans of the sample).

In yet further embodiments, the instructions, criteria and code segments are such as to further perform the method steps of storing other spectral information and such resolving further includes instructions, criteria and code segments for evaluating each non-conformity with the other spectral information to determine if the other information relates to the non-conformity and the resolution of the non-conformity and if it is determined that the other information relates, then applying a corrective action related to the other information.

In yet further embodiments, the instructions, criteria and code segments are such as to further perform the method steps of: before acquiring the sample spectrum, providing a message to a user that instructs the user to take the actions to acquire the sample spectrum; and after acquiring the sample spectrum, analyzing the one or more sample scans or sample spectrum in conjunction with one of the pre-existing background reference spectrum or a modified pre-existing reference spectrum so as to yield a corrected sample spectrum. Additionally, such instructions, criteria and code segments are such as to further perform the method step(s) of, after said analyzing is performed, providing results of such analyzing to the user. Also, such providing further includes instructions, criteria and code segments for displaying the results to the user.

In the foregoing described aspects/embodiments, the different aspects/embodiments of the present invention are directed to applications involving FTIR spectroscopy or FTIR-ATR spectroscopy techniques. However, as indicated herein, this shall not be limiting as it is within the scope of the present invention for the methodology of the present invention be adapted for use with other spectroscopic techniques. Such other spectroscopic techniques include, but are not limited to Diffuse reflectance spectroscopy, Hadamard spectroscopy, fluorescence spectroscopy, and ellipsometry. More specifically, such other spectroscopic techniques can be adapted to use any of the methods described herein above and the devices or apparatuses implementing such other spectroscopic techniques also can be configured so as to embody applications programs that can perform the above described functions.

In more particular aspects/embodiments, such other spectroscopic techniques are adapted or modified so as to include method steps for establishing the acceptability to continue to use a pre-existing reference spectrum that is available for use with such other spectroscopic techniques as well as a methodology for determining how to modify such a pre-existing reference spectrum for continued use or under what conditions one should acquire another reference spectrum. Such a process also is such as to allow other aspects of these other spectroscopic techniques, such as when and how to acquire scans and a spectrum of a sample of interest, to be performed in a manner consistent with these other techniques. As also indicated herein, such methods of the present invention also are such as to allow the methods of the present invention to be carried out either before or after acquiring such sample scans of the sample of interest.

In more particular aspects/embodiments, such other spectroscopic techniques are adapted or modified so as to either undertake a process for determining the acceptability of a pre-existing reference spectrum before acquiring one or more scans of the sample or undertake a similar process for determining the acceptability of a pre-existing reference spectrum after first acquiring the one or more scans of the sample. As described further herein, either process for determining the acceptability of the pre-existing reference spectrum also includes resolving any spectral non-conformities with the pre-existing reference spectrum identified during such a process as herein further described. In the discussion herein, reference to determining the acceptability of a pre-existing reference spectrum shall be understood to include determining the acceptability of a pre-existing reference spectrum that has been modified (i.e., modified pre-existing spectrum or modified reference spectrum) using the methodology of the present invention.

In more particular aspects, such a method is directed to reducing frequency of taking background or reference spectra when using such spectroscopic techniques. More particularly, such a method either (a) undertakes a process for determining the acceptability of a pre-existing reference spectrum before acquiring one or more scans of the sample or (b) undertakes a process in which the one or more scans of the sample are acquired first and then continues with performing a similar process for determining the acceptability of a pre-existing reference spectrum. As described further herein, either process for determining the acceptability of the pre-existing reference spectrum also includes resolving any spectral non-conformities with the pre-existing reference spectrum identified during such a process.

In this regard reference should be made to the discussion regarding the terms "resolve, resolvable, resolving and the like" as it also applies here.

In more particular aspects/embodiments, such determining the acceptability of the pre-existing reference spectrum also includes acquiring a present reference scan; and comparing the present reference scan and the pre-existing reference spectrum to determine if there are any non-conformities there between. If one or more non-conformities are found between the present scan and the pre-existing reference spectrum, such a method includes determining if the one or more non-conformities are resolvable or not. If the one or more non-conformities are resolvable; then resolving each non-conformity in a manner determined to resolve the one or more non-conformities; and if the one or more non-conformities are not resolvable, then acquiring a new reference spectrum using any of a number of techniques as are known to those skilled in the art.

In further embodiments, such resolving further includes evaluating each non-conformity so as to determine if any of the non-conformities corresponds to a simple spectral artifact and not taking any action to correct for such simple spectral artifacts.

In yet further embodiments, such a method further includes storing one or more spectral shapes that are associated with one or more given spectral effects; and such resolving further includes comparing the one or more stored spectral shapes with the identified one or more non-conformities to determine a relationship between a given stored spectral shape and a particular non-conformity. If a relationship is determined or found, such resolving further includes using the stored spectral shape to determine a corrective action to resolve the non-conformity.

In yet further embodiments, such a method further includes storing other spectral information (e.g., algorithm, calculation, calibration information, graphical relationship, data or the like that can be used —alone or in combination- to correct, compensate for or otherwise address an identified non-conformity) and such resolving further includes evaluating each non-conformity with the other spectral information to determine if the other information relates to the non-conformity and the resolution of the non-conformity. If it is determined that the other information relates to the non-conformity, then such resolving also includes applying a corrective action related to the other information to resolve the non-conformity.

In yet further embodiments, such determining if the non-conformities are resolvable includes comparing spectrums for each of the present reference scan and the pre-existing reference spectrum to identify the spectral region(s) exhibiting a non-conformity; comparing each identified non-conformity with saved spectral information to determine if the non-conformity is one of environment related, instrument related or spectral related; and determining if the non-conformity with the pre-existing reference spectrum is resolvable by adjusting the pre-existing spectrum based on the saved information and the present reference scan. If such determining determines that the pre-existing reference spectrum is resolvable, then the process proceeds with adjusting the pre-existing reference spectrum.

In yet further embodiments, where such other spectroscopy technique embodies an ATR interface, such resolving includes evaluating the one or more non-conformities to determine if one or more non-conformities are indicators of a dirty ATR interface. If the ATR interface is determined to be a dirty interface, the process continues with providing an indication to clean the interface.

Such an indication for cleaning can be in any form known in the art including but not limited to, for example, a visual or auditory signal or message, an automatic signal to a device or the like to initiate the cleaning process or a combination thereof. In more particular embodiments, such a visual or auditory signal can be provided to the user to allow the user to manually perform the cleaning process or to start an automated cleaning process. In addition, after cleaning of the interface, such a process includes repeating the steps of acquiring, comparing and determining to determine if the ATR interface is clean.

In yet further embodiments, after cleaning the interface and repeating said determining if one or more non-conformities are indicators of a dirty ATR interface, the process includes determining if this is the first time such a determination is being made. If it is determined that this is not the first time such a determination is being made, then causing the process to proceed to acquiring a new reference sample.

In yet further embodiments, before acquiring the one or more scans of the sample, such a method includes providing a message to a user that instructs the user to take the actions involved with acquiring the sample spectrum; and after acquiring the sample spectrum, analyzing the sample scan(s) in conjunction with one of the pre-existing reference spectrum or the modified pre-existing reference spectrum so as to yield a corrected sample spectrum. Also, after such analyzing is performed, the method includes providing results of such analyzing to the user. In more particular embodiments, such providing includes displaying the results to the user.

In yet more particular embodiments, before acquiring a present reference scan and after determining that a pre-existing reference spectrum is available; such a method includes determining if a predetermined amount of time has elapsed or not since the pre-existing reference spectrum was acquired; if a predetermined amount of time has elapsed then causing the process to proceed to acquiring a new reference spectrum and if a predetermined time has not elapsed then causing the process to proceed with acquiring a present scan and the process that follows for determining the acceptability of the pre-existing reference spectrum or the modified pre-existing reference spectrum.

According to a more particular aspect/embodiments of the present invention such a method for reducing frequency of taking background spectra further includes an alternative mechanism that provides an additional check on the acceptability of a pre-existing reference spectrum or a modified reference spectrum based in part on the pre-existing reference spectrum. As also indicated herein, it also should be recognized that it is within the scope of the present invention for such a methodology to be embodied in an applications program.

In further aspects/embodiments, such a methodology further includes determining if a predetermined amount of time has elapsed or not since the pre-existing reference spectrum was acquired. In the case where a predetermined amount of time has elapsed, then the process is caused to proceed to acquiring a new reference spectrum and thereafter acquiring one or more scans of the sample. In other words, after a sufficient amount of time has elapsed it is presumed that the pre-existing reference spectrum has become stale and thus should not be used any further. On the other hand, if a predetermined time has not elapsed then the process proceeds to the step of acquiring a present reference scan.

In yet further aspects/embodiments, such a methodology further includes determining if a predetermined amount of time has elapsed or not since a check was made of the acceptability of the pre-existing reference spectrum or the modified pre-existing reference spectrum. In this example, the methodology is arranged so that it continues to perform sample scanning while using the pre-existing reference spectrum or modified reference spectrum that was first checked using such a methodology. In the case where a predetermined amount of time has elapsed, then the process is caused to re-check or again check the pre-existing reference spectrum or modified reference spectrum. Using this process the methodology determines if it is acceptable to continue using the reference spectrum it had been using or if a new reference spectrum should be acquired or if the reference spectrum that was being used should be modified or further modified. On the other hand, if the predetermined time has not elapsed then the process continues using the reference spectrum that was being used and also to continue with acquisition of one or more sample scans.

According to another aspect of the present invention where the acceptability of a pre-existing reference spectrum is assessed or determined before acquiring one or more scans of the sample, such a method for reducing the frequency of taking background or reference spectra includes determining if there is a pre-existing reference spectrum available and acquiring a present reference scan before acquiring a sample scan. It should be recognized, however, that such a method can be adapted to perform such a method after acquiring a sample scan as herein described. The method continues with comparing the present reference scan with the pre-existing reference spectrum to determine if the pre-existing reference spectrum is acceptable for further use. More particularly, the present reference scan and the pre-existing reference spectrum are compared to determine if, there are any (e.g., one or more) non-conformities between the two and to identify such non-conformities. If there are no non-conformities found between the present scan and the pre-existing reference spectrum, then the process continues with acquiring a sample scan for a the sample of interest.

If on the other hand one or more non-conformities is/are found between the present scan and the pre-existing reference spectrum, then the process continues with determining if the identified non-conformity/non-conformities is/are resolvable or not. If resolvable, then the process updates the pre-existing reference spectrum (if required) in a manner that is determined to resolve the one or more non-conformities, and the process continues with acquiring the sample scan.

In yet further embodiments, such a method continues with analyzing each identified non-conformity to determine if the non-conformity corresponds to a simple spectral anomaly (e.g., water absorption within a known absorption wavelength range). If it is determined that a non-conformity is a simple spectral anomaly, the process continues with eliminating or ignoring the presence of such simple spectral artifacts. In other words, the pre-existing reference spectrum is not corrected to account for the effect of the simple spectral anomaly.

In yet further embodiments, such a method further includes fitting spectral shapes to the non-conformity to determine if the non-conformity can be adjusted, eliminated or otherwise dealt with using such a spectral shape and information associated with the spectral shape. If it is determined that a non-conformity corresponds to such a spectral shape, the process continues with compensating for or resolving each non-conformity based on the fitted spectral shape(s), the related information and the pre-existing reference spectrum.

In further embodiments, other information such as algorithms, calculations, calibration information and the like is made available and the non-conformity is evaluated using such other information. From such an evaluation, it is determined how to resolve or compensate for one or more non-conformities using such information. Thereafter, the pre-existing reference spectrum can be adjusted or compensated for using the applicable other information.

In yet further embodiments, a resultant reference spectrum is created using such information resolving or compensating for a non-conformity. Such a resultant reference spectrum is preferably saved and replaces the pre-existing reference spectrum for future sample scanning purposes (e.g., becomes a modified pre-existing reference spectrum or modified reference spectrum).

In further embodiments, such as when the particular spectroscopy technique being used embodies an ATR interface, the process also continues with determining if the ATR interface is clean or not. If it is determined that that one or more identified non-conformities suggest that the ATR interface might be dirty, then the process continues with causing the cleaning of the ATR interface. As indicated herein, in more particular aspects/embodiments, if the ATR interface is determined to be a dirty interface, the process continues with providing an indication to clean the interface. Such an indication for cleaning can be in any form known in the art including but not limited to, for example, a visual or auditory signal or message, an automatic signal to a device or the like to initiate the cleaning process or a combination thereof. In more particular embodiments, such a visual or auditory signal can be provided to the user to allow the user to manually perform the cleaning process or to start an automated cleaning process.

According to a more particular aspect/embodiments of the present invention such a method for reducing frequency of taking background spectra further includes an alternative mechanism that provides an additional check on the acceptability of a pre-existing reference spectrum or a modified reference spectrum that is based in part on the pre-existing reference spectrum. As also indicated herein, it also should be recognized that it is within the scope of the present invention for such a methodology to be embodied in an applications program.

In further aspects/embodiments, such a methodology further includes determining if a predetermined amount of time has elapsed or not since the pre-existing reference spectrum was acquired. In the case where the predetermined amount of time has elapsed, then the process is caused to proceed to acquiring a new reference spectrum and thereafter acquiring one or more scans of the sample. In other words, after a sufficient amount of time has elapsed it is presumed that the pre-existing reference spectrum has become stale and thus should not be used any further. On the other hand, if a predetermined time has not elapsed the causing the process proceeds to the step of acquiring a present reference scan before acquiring a sample spectrum.

In yet further aspects/embodiments, such a methodology further includes determining if a predetermined amount of time has elapsed or not since a check was made of the acceptability of the pre-existing reference spectrum or the modified pre-existing reference spectrum. In this example, the methodology is arranged so that it continues to perform sample scanning while using the pre-existing reference spectrum or modified reference spectrum that was first checked using such a methodology. In the case where a predetermined amount of time has elapsed, then the process is caused to re-check or again check the pre-existing reference spectrum or modified reference spectrum. Using this process the methodology determines if it is acceptable to continue using the reference spectrum it had been using or if a new reference spectrum should be acquired or if the reference spectrum that was being used should be modified or further modified. On the other hand, if the predetermined time has not elapsed then the process continues using the reference spectrum that was being used and also to continue with acquisition of one or more sample scans.

According to another aspect/embodiment, there is featured an applications program for execution on a logic circuit including a digital processor or microprocessor. According to yet another aspect of the present invention, there is featured a non-transitory computer medium on which is stored an applications program for execution on a logic circuit including a digital processor or microprocessor. According to still yet another aspect of the present invention, there is featured a computer system including a logic circuit such as digital processor and an applications program for execution on the logic circuit. In embodiments, such a computer system further includes a storage medium operable coupled to the logic circuit, where the applications program is stored on the storage medium.

In further aspects/embodiments, such an applications program includes instructions, criteria and code segments for performing a methodology including the steps of the present invention such as that described hereinabove. More specifically such a method includes processes for reducing frequency of taking background or reference spectra when using such other spectroscopic techniques and even more particularly, either (a) undertakes a process for determining the acceptability of a pre-existing reference spectrum before acquiring one or more scans of the sample or (b) undertakes a process in which the one or more scans of the sample are acquired first and then performs a similar process for determining the acceptability of a pre-existing reference spectrum or modified reference spectrum. As described further herein, either process for determining the acceptability of the pre-existing reference spectrum or modified reference spectrum also includes resolving any spectral non-conformities with the pre-existing reference spectrum or modified reference spectrum identified during such a process.

Other aspects and embodiments of the invention are discussed below.

DEFINITIONS

The instant invention is most clearly understood with reference to the following definitions:

USP shall be understood to mean U.S. Patent Number and U.S. Publication No. shall be understood to mean U.S. Published Patent Application Number.

FTIR shall be understood to mean Fourier Transform Infrared Spectroscopy which is a well-known technique used to obtain infrared spectra of absorption, emission or Raman scattering of a solid, liquid or gas. In use, an FTIR spectrometer simultaneously collects spectral data in a wide spectral range and a Fourier transform (a mathematical process) is used to convert the raw data into the actual spectrum. In Fourier transform spectroscopy, a broadband beam containing many frequencies of light is used and one measures how much of that beam is being absorbed such as by the sample. Next, the beam is modified to contain a different combination of frequencies, giving a second data point. This process is repeated as many times as necessary and a computer deconvolves the acquired spectral data to infer what the absorption is at each wavelength.

ATR shall be understood to mean attenuated total reflectance which is a sampling technique used in conjunction with infrared spectroscopy which enables samples to be examined directly in the solid or liquid state without further preparation. For example, a liquid sample would be applied to the surface of an ATR interface.

The term "scan" shall be understood as generally being descriptive of the process involving the collection of a single interferogram, as would be generated, for example, by one movement of the moving mirror of an interferometer (e.g., a Michelson interferometer). It should be recognized that that this example is not limiting as a scan shall be understood to be generally describing the process of acquiring a set of spectral data using a broad beam technique, where the beam is composed of different wavelengths. The phrase/term "complete scan of a sample" or the like shall be understood to be describing a process where one or more scans are acquired such that the resultant signal-to-noise ratio for the acquired spectral data is acceptable. In addition the term "spectrum" shall be understood to be the resultant of the process performed by a computer or other digital processing device which deconvolves the acquired spectral data to infer what the absorption is at each wavelength for the scanned sample or background. As indicated herein, the acquired spectral data can be from one scan, a predetermined number of scans (such as is done for the background or reference spectrum) or a number of scans such that the resultant signal-to-noise ratio is acceptable.

The term/phrase "reference spectrum" shall be understood to be referring to an absorption spectrum taken without a sample and that reflects external environmental conditions (e.g., carbon dioxide, water vapor, etc.) which can appear in the measured spectrum, reflects optical effects attributable to the device measuring and detecting optical signals (e.g., instrument effects such as those caused by heating/cooling of optical components) as well as reflecting other effects that can be attributed to the background environment or measuring device.

The terms "comprising" and "including: as used in the discussion directed to the present invention and the claims are used in an open-ended fashion and thus should be interpreted to mean "including, but not limited to." Also the terms "couple" or "couples" is intended to mean either an indirect or direct connection. Thus, if a first component is coupled to a second component, that connection may be through a direct connection, or through an indirect connection via other components, devices and connections. Further the terms "axial" and "axially" generally mean along or substantially parallel to a central or longitudinal axis, while the terms "radial" and "radially" generally mean perpendicular to a central, longitudinal axis.

Additionally directional terms such as "above," "below," "upper," "lower," etc. are used for convenience in referring to the accompanying drawing figures. In general, "above," "upper," "upward" and similar terms refer to a direction toward a proximal end of an instrument, device, apparatus or system and "below," "lower," "downward," and similar terms refer to a direction toward a distal end of an instrument, device, apparatus or system, but is meant for illustrative purposes only and the terms are not meant to limit the disclosure.

A computer readable medium shall be understood to mean any article of manufacture that contains data that can be read by a computer or a carrier wave signal carrying data that can be read by a computer. Such non-transitory computer readable media includes but is not limited to magnetic media, such as a floppy disk, a flexible disk, a hard disk, a solid state hard drive, reel-to-reel tape, cartridge tape, cassette tape or cards, FLASH drives, USB drives, solid state hard drives or other media using nonvolatile RAM; optical media such as CD-ROM and writeable compact disc; magneto-optical media in disc, tape or card form; or paper media, such as punched cards and paper tape. Such transitory computer readable media includes a carrier wave signal received through a network, wireless network or modem, including radio-frequency signals and infrared signals.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 1A:
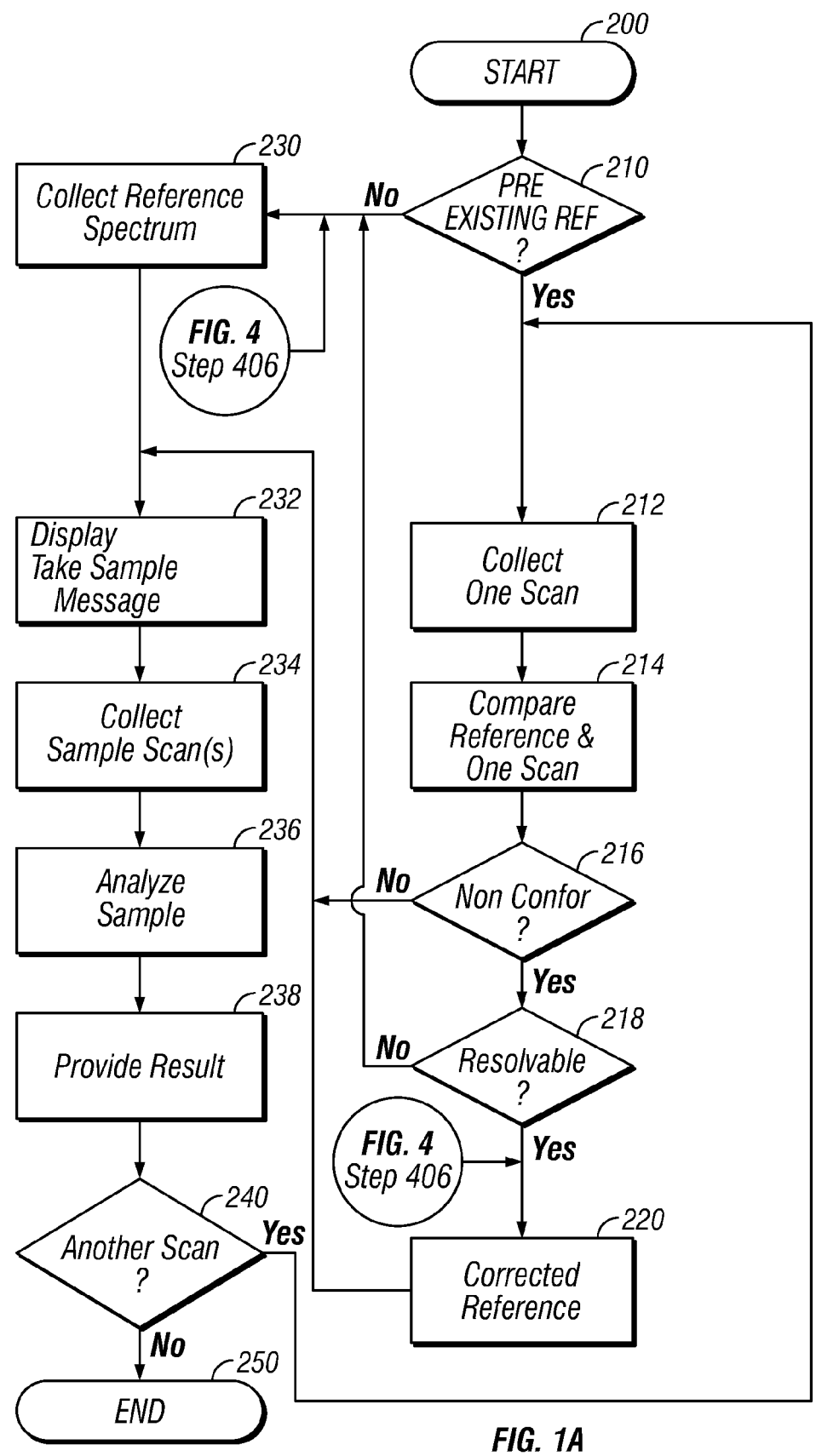
FIG. 1A is a high level flow diagram or flow chart illustrating a methodology or applications program logic according to one aspect or embodiment of the present invention and for use with FTIR spectroscopy techniques.

As indicated herein, the methods and software application programs of the present invention can be embodied in any of number of measurement devices, apparatuses or systems as known in the art including that described herein which apparatuses/devices can be used for any of a number of sample identification applications. As further described herein, such measurement devices, apparatuses or systems embody a digital processor, a microprocessor, digital signal processor, or other logic circuits (e.g., ASIC or PGM circuitry) as are known or hereinafter developed on which a software applications program according to the present invention can be executed so as to carry out the method steps and logics of the present invention. Hereinafter, the term measurement device or devices is used for convenience, however, this shall not be construed as limiting the invention.

Such methods and applications programs of the present invention, as well as the measurement devices embodying such methods and applications programs can be used in airports and other transportation hubs, in government buildings, and in other public places to identify unknown (and possibly suspicious) substances, and to detect hazardous and/or prohibited substances. Airports, in particular, restrict a variety of substances from being carried aboard airplanes. Such methods and applications programs and measurement devices embodying same can be used to identify substances that are discovered through routine screening of luggage, for example. Identified substances can be compared against a list of prohibited substances (e.g., a list maintained by a security authority such as the Transportation Safety Administration ("TSA") to determine whether confiscation and/or further scrutiny by security officers is warranted.

In addition, law enforcement officers can use such methods, applications programs and portable measurement devices embodying same, to identify unknown substances, including illegal substances such as narcotics. Accurate identifications can be performed in the field by on-duty officers. In addition, firefighters, people dealing with hazardous materials, department of public works personnel and the like can use such methods, applications programs and portable measurement devices embodying same, to identify unknown substances or confirm the identity of labeled substances during their respective operations. More specifically, as these operations may be conducted when time is of the essence, use of such methods, applications programs and portable measurement devices embodying same can allow law enforcement, firefighters or other safety personnel to quickly and accurately identify substances in the field. This thereby reduces the potential hazard to these people in the field as well as to the general public. This also allows, such people to quickly determine the appropriate response to take at the earliest time possible.

Such methods, applications programs as well as measurement devices that embody same, also can be used to identify a variety of industrial and pharmaceutical substances. Shipments of chemicals and other industrial materials can be quickly identified and/or confirmed on piers and loading docks, prior to further transport and/or use of the materials. Further, unknown materials can be identified to determine whether special handling precautions are necessary (for example, if the materials are identified as being hazardous). Pharmaceutical compounds and their precursors can be identified and/or confirmed prior to production use and/or sale on the market. As also indicated herein, such materials can be quickly identified under hazardous conditions (e.g., fire, transportation accident, etc.), especially were time is critical.

Generally, a wide variety of different samples (e.g., liquids and solids) can be identified using the methods and applications programs of the present invention as well as measurement devices embodying same. Such samples include for example: pharmaceutical compounds (and precursors thereof); narcotics; industrial compounds; explosive, energetic materials (e.g., TNT, RDX, HDX, and derivatives of these compounds); chemical weapons (and portions thereof); household products; plastics; powders; solvents (e.g., alcohols, acetone); nerve agents (e.g., soman); oils; fuels; pesticides; peroxides; beverages; toiletry items; other substances (e.g., flammables) that may pose a safety threat in public and/or secure locations; and other prohibited and/or controlled substances.

In its broadest aspects, the present invention features a device(s), apparatus(s), system(s), applications programs, and/or method(s) relating to any of a number of spectroscopic techniques. In more particular aspects/embodiments, there are featured a device(s), apparatus(s), system(s), applications programs, and/or method(s) relating to FTIR spectroscopy or FTIR-ATR spectroscopy. Even more particularly, there is featured a method for reducing frequency of taking background or reference spectra when using FTIR spectroscopy or FTIR-ATR spectroscopy. In more particular aspects, such a method either (a) undertakes a process for determining the acceptability of a pre-existing reference spectrum or a modified reference spectrum before acquiring one or more scans of the sample or (b) undertakes a similar process for determining the acceptability of a pre-existing reference spectrum after first acquiring the one or more scans of the sample. As described further herein, either process for determining the acceptability of the pre-existing reference spectrum also includes resolving any spectral non-conformities with the pre-existing reference spectrum identified during such a process as herein further described. In the discussion herein reference to determining the acceptability of a pre-existing reference spectrum shall be understood to include determining the acceptability of a pre-existing reference spectrum that has been modified (i.e., modified pre-existing spectrum or modified reference spectrum) using the methodology of the present invention.

Referring now to the various figures of the drawing wherein like reference characters refer to like parts or method steps, there is shown in FIGS. 1-4 various high level flow diagrams or flow charts illustrating methodologies or applications program logic according to a number of aspects and/or embodiments of the present invention and that are particularly suitable for use with FTIR or FTIR-ATR spectroscopy techniques. Although such methods are illustrated when undertaking a process for determining the acceptability of a pre-existing reference spectrum or a modified reference spectrum before acquiring one or more scans of the sample, this shall not be limiting because as further described herein, such methodologies can be easily adapted so as to undertake a similar process for determining the acceptability of a pre-existing reference spectrum after first acquiring the one or more scans of the sample.

These flow diagrams/flow charts, illustrate the structure or the logic of the present invention as embodied in computer program software for execution on a computer, digital processor, microprocessor, digital signal processor or other logic circuits (e.g., application specific integrated circuit—ASIC; programmable gate arrays—PGA) as are known in the art or hereinafter developed. Those skilled in the art will appreciate that the flow diagrams/flow charts illustrate the structures of the computer program code elements, including logic circuits on an integrated circuit that function according to the present invention. As such, the present invention is practiced in its essential embodiment(s) by a machine component that renders the program code elements in a form that instructs a digital processing apparatus (e.g., computer, microprocessor, digital processor) to perform a sequence of function step(s) corresponding to those shown in the flow diagrams.

In the following reference is made to the methodology or methodologies of the present invention for convenience. However any such reference, shall not be understood to be limiting the present invention and thus any such reference shall be understood to also include an applications program including instructions, criteria and code segments for carrying out or implementing such methodologies (e.g., such as by using a digital processing device) as well as a system, apparatus or device having such a digital processing device and such an applications program.

According to further aspects/embodiments, the present invention also features a computer readable storage medium on which is stored an applications program according to the present invention that more particularly includes instructions, criteria and/or code segments for carrying out the steps of the methodologies as herein described and embodied in such applications programs. Such a computer readable storage medium includes a storage medium that is useable in conjunction with a processor or the like (e.g., RAM, magnetic hard disk, solid state hard drive, optical disk) or a portable storage medium useable for transporting such an application (s) for later downloading (e.g., optical disk, magnetic media disks, a USB type of drive, a FLASH type of drive or a so-called external hard drive). In more particular embodiments, such storage media or computer readable media are non-transitory.

While the present invention is described hereinafter from the start of the method (STEP 200—FIGS. 1A, 1B, 2A, 2B), it also is contemplated that steps or processes can be taken prior to or preceding implementation of the methodology to completely scan a sample. These prior steps or processes include those taken involving calibration, maintenance or upkeep of a measurement device embodying such a methodology or application program. In addition, when the methodology is configured so as to undertake a process for determining the acceptability of a pre-existing reference spectrum after first acquiring the one or more scans of the sample, such acquiring of the sample scans can be arranged so as to occur before or after start of the method (Step 200). This will be described further herein.

When the measurement device or spectroscopy technique being used includes an ATR interface it also is common for the measurement device to be configured so it displays or otherwise provides a message or other reminder to the user or operator to remind them to take the appropriate actions to assure the ATR interface is clean before scanning a sample. In yet further embodiments, a signal can be generated that automatically causes the cleaning process to be performed. For example, such steps or processes for cleaning can include, for example, a visual inspection of the ATR interface or the crystal forming such an interface to evaluate the cleanliness of the interface. If it is determined from the visual inspection, for example, that the interface appears unclean, the appropriate steps for cleaning the interface are taken as well as re-inspecting the interface following such cleaning. It should be recognized that such cleaning actions also can be performed as a matter of procedure or rote after a sample scan is performed or before scanning a sample is undertaken, even if a visual inspection does not appear to show a need to clean the interface.

Notwithstanding such efforts to clean the ATR interface prior to use, it is possible that these efforts may prove to be insufficient. Accordingly, and as described below in connection with the methodologies for use with FTIR-ATR spectroscopy techniques, such methodologies also are adaptable to include processes for automatically assessing or evaluating the cleanliness of the ATR interface and so appropriate actions can be taken when needed. In the case where the methodology is directed to an "other spectroscopic technique" which also embodies an ATR interface, the foregoing also could apply to that other technique.

In addition, such pre-use or pre-sample scanning steps can include those for purposes, for example, of acquiring a reference spectrum and saving the acquired reference spectrum even though scanning is not presently contemplated. Such a reference spectrum can be obtained using any of a number of techniques known to those skilled in the art and otherwise appropriate for the intended use including those described herein.

In embodiments of the present invention, such starting of the methodology (Step 200) also is contemplated as involving a positive action on the part of the user or operator to initiate the methodology. Such actions of the user include turning the measurement device ON or if the device is already ON, actuating a button, switch or other functionality of the measurement device associated with initiating the process/methodology of the present invention or making a keystroke using an input device (e.g., the display) that is associated with initiating the process/methodology of the present invention.

Referring now to FIG. 1A, there is shown a high level flow diagram or flow chart illustrating a methodology or applications program logic according to one aspect or embodiment of the present invention. More specifically and as further described herein, such a methodology or applications program logic is particularly suitable for use in connection with measurement devices, apparatuses or systems that are configured for carrying out FTIR spectroscopy techniques when scanning a sample of interest. However, as further described herein such a methodology can be easily adapted for use with any of a number of other spectroscopic techniques known to those skilled in the art including but not limited to Diffuse reflectance spectroscopy, Hadamard spectroscopy, fluorescence spectroscopy, and ellipsometry. Also and as described further herein, such a methodology or applications program logic is particularly suitable for resolving or compensating for a wide range of non-conformities between an initial reference or background scan (i.e., One Scan) and a pre-existing reference spectrum.

In this regard it should be understood that the terms "resolve, resolvable, resolving and the like" are used herein to generally describe or cover whatever means, algorithm, calculation, calibration information, graphical relationship, data or the like that can be used (alone or in combination) to correct, compensate for or otherwise address an identified non-conformity using the methodology of the present invention. Therefore, the use of such a term in combination with another term or phrase such as for example, compensating or correcting, shall not be considered as limiting the term resolve or the like.

Such resolving or compensating can include adjusting the pre-existing reference spectrum to compensate for the identified non-conformities. An exemplary process is more particularly described in connection with the discussion for FIG. 4. Such non-conformities also might identify a concern or issue that could arise while acquiring the sample scan which would need to be accounted or compensated for, such as during the analysis phase of the sample scan/spectrum. In such a case, the methodology or applications program can further include a process for identifying or determining the appropriate correction factor, algorithm calculation or the like to address the identified issue or concern, and then causing same to be applied as compensation to the sample scan or sample spectrum or to the corrected reference spectrum. In this way, the methods and applications programs of the present invention can compensate for identified non-conformities between the acquired One Scan and the pre-existing reference spectrum as well as for other concerns or issues that the non-conformities indicate could occur while acquiring spectral data during the sample scan process.

Now referring back to the methodology of FIG. 1A, after starting the methodology or process flow (Step 200), the process/methodology proceeds with determining if a reference spectrum has been saved or not. In other words, is there a pre-existing reference spectrum available or not for use (Step 210). It also is contemplated that the methodology of the present invention can further include a step or process under the control of the user, which allows the user to override the planned process and cause the methodology to proceed along a different logic path. For example, the user may believe that the stored reference spectrum is stale or otherwise un-useable for any of a number of reasons and also that the process should thus proceed with acquiring a new reference spectrum. In such a case, the user could actuate a button, switch or a virtual button/key on a display that causes the process to proceed with acquiring a new reference spectrum even though the user knows that a pre-existing reference spectrum is stored and thus available. If such an action was taken, then the process would proceed to the process for collecting or acquiring a new reference spectrum (Step 230).

If it is determined that there is no pre-existing reference spectrum available (NO, Step 210) then the process flow proceeds to the process for collecting or acquiring a new reference spectrum (Step 230). On the other hand, if there is a reference spectrum available (YES, Step 210) then the process flow proceeds to the process or method steps for determining if the pre-existing reference spectrum is appropriate or suitable for continued use in connection with the analysis of a sample. In other words, the process determines if it is okay to continue using the pre-existing reference spectrum in connection with the analysis of the spectrum for a sample. If this process ultimately determines that the pre-existing reference spectrum is suitable for continued use, then the process can avoid the need to perform the lengthy process of acquiring N scans (e.g., N being ≥8) of spectral data and converting the acquired spectral data to a create another reference spectrum. In this way, the methodology of the present invention can avoid the existing practice of automatically acquiring and thus creating a reference spectrum closer in time to the acquisition of spectral data representative of the sample.

After determining that there is a pre-existing reference spectrum available (YES, Step 210), the process proceeds with acquiring one scan of spectral data under reference or background collection conditions (Step 212). In other words, spectral data is acquired without a sample being coupled to the measurement device and under conditions one would expect when collecting spectral data for a reference spectrum. In more particular embodiments, only one scan of spectral data is acquired, however, additional scans may be acquired if deemed necessary. Hereinafter, the term "One Scan" shall be understood to be referring to one scan of spectral data acquired in this particular process step.

The spectral data acquired during the One Scan is compared to the pre-existing reference spectrum (Step 214) so an initial determination can be made as to whether the pre-existing reference spectrum is okay for further use. In other words, the pre-existing reference spectrum and the One Scan are compared to determine if there are any non-conformities between the reference spectrum and the One Scan (Step 216). If there are no nonconformities identified, (NO, Step 216) then the process proceeds with the process for acquiring and analyzing the spectrum for a sample of interest (Steps 232-238) as described further herein.

If there are identified non-conformities (YES, Step 216), then the process proceeds with determining if the non-conformities are of the type and nature which make them resolvable or not (Step 218). Thus, the process proceeds with evaluating and resolving or compensating for any identified non-conformities such as using a process like that described further herein in connection with FIG. 4. If these non-conformities are of the type which can be resolved or compensated for, the process continues with resolving or compensating for the non-conformities in the appropriate manner. This can include for example, determining if and how the reference spectrum should be adjusted to resolve or compensate for an identified non-conformity as well as how one should make an adjustment or compensation to an acquired sample spectrum.

As described further herein, such resolving and compensating can include a determination that the pre-existing reference spectrum should be modified to resolve or compensate for one or more of the non-conformities as well as the way in which to modify the reference spectrum. As noted herein such a process also can determine that the non-conformity is an indication of a concern or issue that is more properly addressed by taking action later in connection with the analysis of the acquired sample spectrum. For example, if one wavelength subset that is a subset of the wavelength range of the entire reference scan is found to be unusually attenuated, say because of high water absorption or because of spectrometer misalignment, then that wavelength subset might be given lesser weight in the peak-matching algorithm that compares the collected sample spectrum to the library spectra in order to identify the sample.

As further described herein, this process also can determine that the non-conformity is of a nature that no action need be taken to correct or compensate for it (e.g., noise, water absorption within a known absorption wavelength range), in other words, the non-conformity is per se resolvable. Thus, if all of the identified non-conformities requiring action are deemed resolvable (YES, Step 218), then the process proceeds with correcting the reference spectrum—as needed (Step 220) and then proceeds to the process for acquiring a sample spectrum and analyzing it (Steps 232-238). In the case where the resolution or compensation involves the sample spectrum, such resolving or compensating would be identified for later resolution and addressed for example, during the sample acquiring and analysis phase of the process.

If, on the other hand, it is determined that the non-conformities cannot be resolved or compensated for (NO, Step 218) then the process proceeds to the process for collecting or acquiring a new reference spectrum (Step 230).

After acquiring a new reference spectrum (Step 230) or after determining that the nonconformities are resolvable and updating the reference spectrum accordingly (Steps 218, 220), the process proceeds with acquiring and analyzing the spectrum for a sample of interest. Such a process can include informing the user that it is time to scan the sample or to initiate the process for obtaining a sample spectrum (Step 232). For example, a message can be displayed to the user on the measurement device (e.g., a display for such a device), where the message indicates that it is time to take the sample (Step 232). In other words, the process has advanced to the point that one can proceed with acquisition of spectral data and analysis for the sample of interest.

Upon receiving such a message and depending upon the measurement device's construction, the user would take the appropriate steps to correctly dispose, mount or couple the sample of interest to the provided measurement device particularly to one that is capable of using a FTIR spectroscopy technique. In other words, the user or operator would take the appropriate actions necessary so that the sample is appropriately coupled to the measurement device so that sampling can be performed.

After so mounting/coupling the sample and the measurement device, the process proceeds to acquiring or collecting the spectral data for the sample (Step 234) according to the appropriate spectroscopy technique. As described herein and as known to those skilled in the art, in FTIR spectroscopy, a broadband beam (i.e., beam containing many frequencies of infrared light is shined on the sample, and one detects and measures how much of that broadband beam is being absorbed (e.g., absorbed by the sample). If necessary, the beam is modified to contain a different combination of frequencies (e.g., movable mirror is moved to another position) thereby yielding another scan of spectral data and thus giving another data point. This process of beam modification and acquiring spectral data is repeated as and as many times as desired or necessary. The number of scans acquired is typically determined based on signal-to-noise considerations. In more illustrative exemplary embodiments the sample is subjected to 1 or more such scans.

After acquiring the spectral data associated with the sample, the spectral data is converted into a spectrum. For example, a digital processor processes the acquired spectral data using any of the techniques known to those skilled in the art) to infer what the absorption is at each wavelength so to yield a spectrum representative of the sample of interest. As is known in the art, a Fourier transform process is used to convert the spectral data into a spectrum. In more specific embodiments, the acquired spectral data is deconvolved to infer what the absorption is at each wavelength so to yield a spectrum representative of the sample of interest.

After converting the sample spectral data, an analysis of the sample spectrum is performed (Step 236). Such an analysis includes removing any spectral effects attributable to the reference spectrum from the acquired sample spectrum, such as effects associated with the environment and the measurement device, so as to yield a spectrum that is representative of the sample itself. As indicated herein such an analysis also would include applying any factors, algorithms or the like to compensate for any effects that could affect sampling that were identified during the evaluation of the One Scan and the pre-existing reference scan (as described above). (Step 236). Such a modified sample spectrum, is herein referred to as a resultant spectrum.

As illustration, in exemplary embodiments, the resultant absorption spectrum (A) is calculated from the sample (S) and reference (B) single beam spectra as $-\log 10(S/B)$. In this way, any multiplicative effect that is common to both S and B will be removed by ratio'ing S to B. Such multiplicative effects include source intensity; transmission or reflection of optical elements in the spectrometer; detector responsivity; reduction in transmission due to water vapor and carbon dioxide absorption in the beam path of the spectrometer. In the case of FTIR-ATR spectroscopy such multiplicative effects also would include reduction in transmission due to an unwanted material on the surface of the ATR crystal (where the sample is placed).

After performing such an analysis, the resultant spectrum is made available or provided to the user or operator of the measurement device (Step 238). As most portable measurement devices are configured with a display, the result is displayed to the user on the measurement device or other optical device or printing apparatus as are known in the art and operably coupled to the measurement device.

As indicated herein, such a measurement device can be further configured with a memory that includes spectrums or spectral data that can be used to compare with the resultant spectrum for purposes of identifying the material composition or make-up of the sample of interest. Therefore, the analysis of the sample of interest can further include determining the composition or make-up of the sample of interest and such providing the resultant to the user or operator, also can include providing the results of the composition or make-up analysis to the user or operator. In this way, the user/operator is provided with the spectrum and/or the chemical make-up of the sample of interest.

It also is within the scope of the present invention, that such analysis and providing the results (Steps 236, 238) can be arranged so that the analysis can determine and categorize the sample of interest as being hazardous (e.g., flammable), dangerous (e.g., explosive) or an illegal substance (e.g., illegal narcotic). It is further contemplated, that the methodology can be arranged so that an appropriate warning accompanies the result being provided so that the user/operator has a further warning as to the potential threat provided by the sample of interest.

After making the result(s) available to the user, the process proceeds with determining if another sample scanning process is to be performed or not (Step 240). If another scanning process is to be done for a new sample (YES, Step 240), then the process proceeds to Step 212, the process of acquiring a new One Scan and continues with the process which follows and as described above. In such a case, there would be a delay provided to allow the user or operator to de-couple the sample from the measurement device and to take any other actions necessary to prepare the device for another scanning process such as, for example, cleaning the surface of the area to which the sample is coupled. If on the other hand, if another sample is not going to be scanned (NO, Step 240), then the process proceeds with ending the process flow or methodology (Step 250).

Figure 1B:
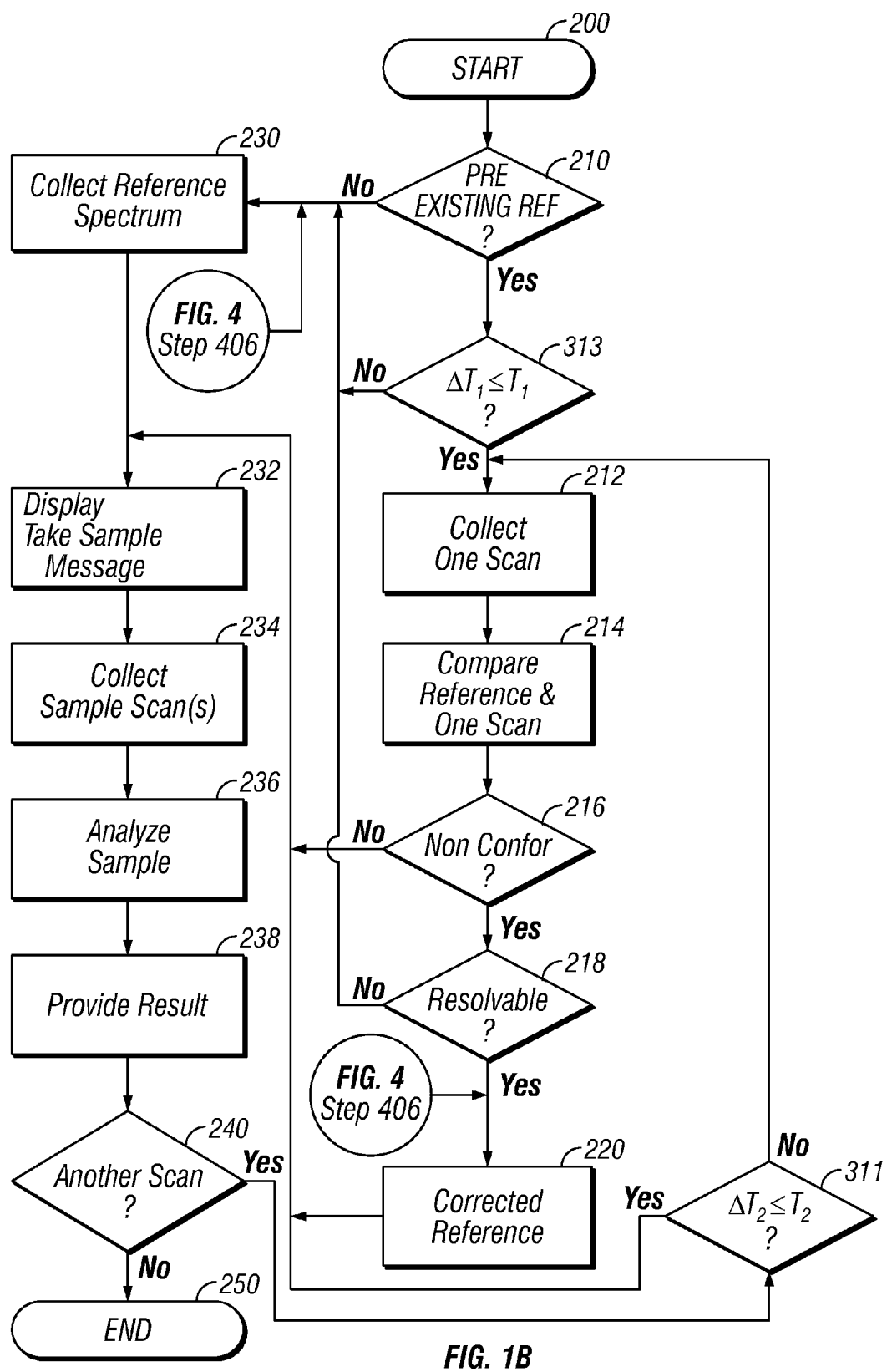
FIG. 1B is another high level flow diagram/flow chart illustrating another methodology or applications program logic according to another aspect or embodiment of the present invention and for use with FTIR spectroscopy techniques.

Referring now to FIG. 1B, there is shown another high level flow diagram or flow chart illustrating another methodology or applications program logic according to another aspect or embodiment of the present invention. More specifically and as further described herein, such a methodology or applications program logic is particularly suitable for use in connection with measurement devices, apparatuses or systems configured for carrying out FTIR spectroscopy techniques when scanning a sample of interest. In more particular aspects, such a method either (a) undertakes a process for determining the acceptability of a pre-existing reference spectrum or a modified reference spectrum before acquiring one or more scans of the sample or (b) undertakes a similar process for determining the acceptability of a pre-existing reference spectrum after first acquiring the one or more scans of the sample.

As described further herein, for either process for determining the acceptability of the pre-existing reference spectrum, such a methodology or applications program logic is particularly suitable for resolving or compensating for a wide range of non-conformities between an initial reference or background scan (i.e., One Scan) and a pre-existing reference spectrum. As indicated herein, the methods and applications programs of the present invention also are such as to compensate for identified non-conformities between the acquired One Scan and the pre-existing reference spectrum as well as for other concerns or issues that the non-conformities indicate could occur while acquiring spectral data during the sample scan process. Also, such a methodology or applications program logic is particularly suitable for controlling (e.g., re-directing) the process flow in cases where it is possible that the pre-existing reference spectrum has become un-useable. Reference shall be made to the foregoing discussion regarding the methodology illustrated in FIG. 1A for those steps having common reference numerals and process steps except as otherwise described hereinafter.

Although the method is illustrated when undertaking a process for determining the acceptability of a pre-existing reference spectrum or a modified reference spectrum before acquiring one or more scans of the sample, this shall not be limiting because as further described herein, such methodologies can be easily adapted so as to undertake a similar process for determining the acceptability of a pre-existing reference spectrum after first acquiring the one or more scans of the sample, which is described further herein.

As indicated herein, there can be circumstances or cases where it would be desirable to bypass the logic process of the methodology or applications program as show in FIG. 1A so that under certain circumstances the process follows another particular given logic pathway. According to the aspect/embodiment of the methodology or applications logic shown in FIG. 1B, such a methodology or applications program logic includes checks to determine if the pre-existing reference spectrum has become un-useable (e.g., as being stale or old) because of the passage of time or if the scanning process has been underway for a sufficient amount of time that would warrant re-checking the acceptability of the pre-existing spectrum or a modified pre-existing spectrum for continued use.

In this regard, after determining that there is a pre-existing reference spectrum available (YES, Step 210), the process proceeds with determining if the time that has elapsed ($\Delta T_1$) since the pre-existing reference spectrum was first saved or stored in the measurement device is less than or equal to a predetermined time—$T_1$, (Step 313). In particular embodiments, the pre-determined time is established so that a spectrum that has been stored for more than $T_1$ is considered to be unacceptable for continued use. In other words, it is believed that conditions have changed sufficiently since the stored pre-existing spectrum was acquired and/or which makes the spectrum suspect as being stale or un-useable. In this way, action to re-direct the process flow can be automatically implemented without having the user or operator to intervene or to go through the process to determine that the pre-existing reference spectrum is not acceptable for continued use and then to re-direct the process so as to acquire a new reference spectrum.

If it is determined that the elapsed time is less than or equal to the predetermined time—$T_1$ (YES, Step 313) then the pre-existing reference spectrum is thereafter evaluated to determine if it acceptable for continued use as described above in connection with FIG. 1A. In such a case, the process proceeds to acquiring a One Scan. If it is determined that the elapsed time is greater than the predetermined time (NO, Step 313), then the process proceeds to Step 230 (FIG. 1A, 2A) and a new reference spectrum is obtained.

As indicated herein, the present methodology also includes a check to determine if the scanning process has been underway for a sufficient amount of time that would warrant re-checking the reference spectrum's acceptability for further use. More particularly, a determination is made to determine if the time that has elapsed ($\Delta T_2$) since scanning first began or the elapsed time since the last scan is less than or equal to a predetermined time—$T_2$, (Step 311). The pre-determined time is established so that if the scanning process has continued for more than a desired period of time, the pre-existing spectrum should be checked to see if it should be replaced or if it is still considered acceptable for continued use. If it is determined that the elapsed time is less than or equal to the predetermined time (YES, Step 311), then the process proceeds to Step 232 (FIG. 1A) and continues with the acquisition of a spectrum of the sample of interest and an analysis of such a spectrum (Steps 232-238). If it is determined that the elapsed time is greater than the predetermined time (NO, Step 311), then the process proceeds to Step 212 and continues with the process for determining the acceptability of the pre-existing reference spectrum for continued use.

Figure 2A:
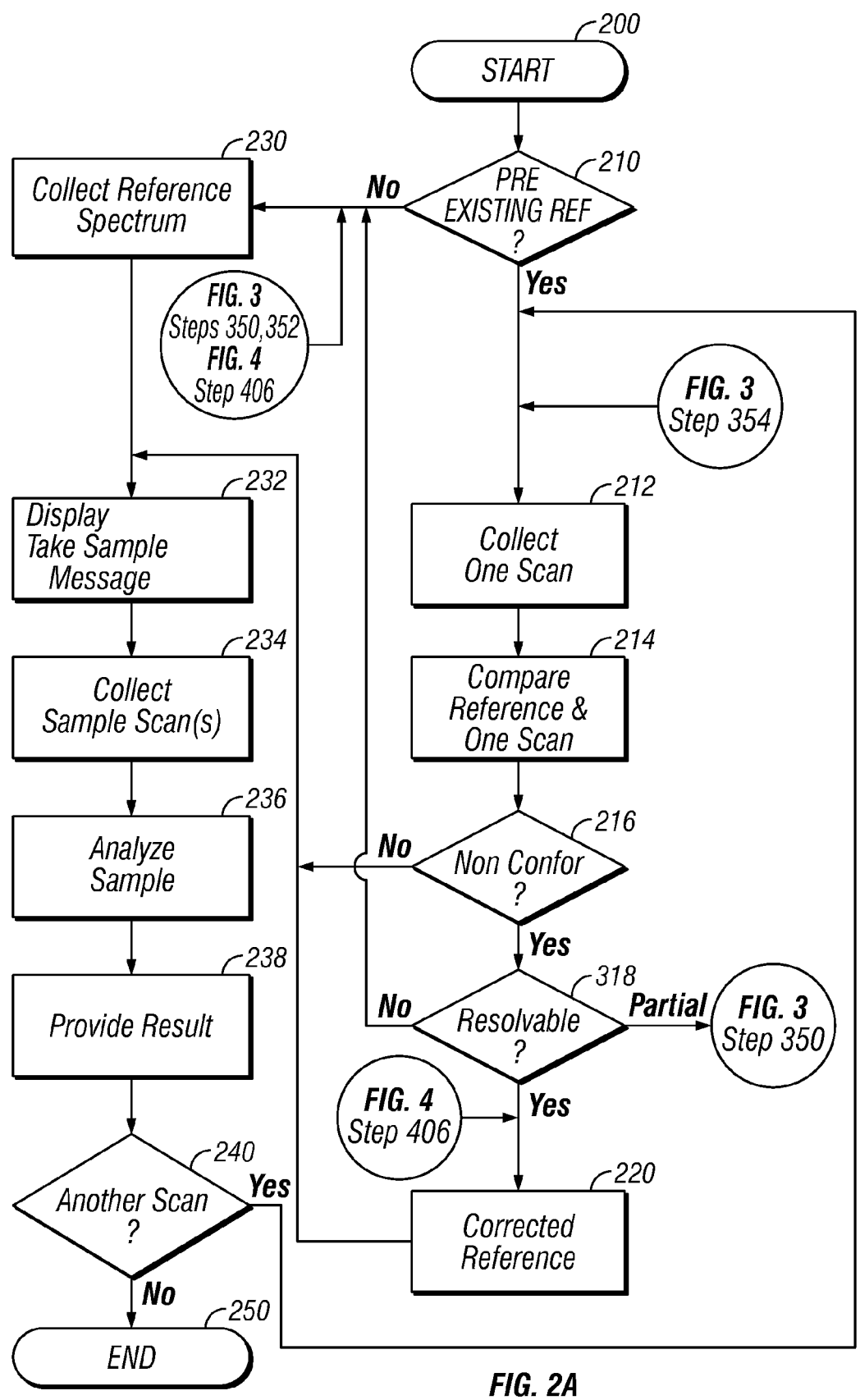
FIG. 2A is a high level flow diagram/flow chart illustrating another methodology or applications program logic according to another aspect or embodiment of the present invention and for use with FTIR-ATR spectroscopy techniques.

Referring now to FIG. 2A, there is shown a high level flow diagram or flow chart illustrating a methodology or applications program logic according to yet another aspect or embodiment of the present invention. More specifically and as further described herein, such a methodology or applications program logic is particularly suitable for use in connection with measurement devices, apparatuses or systems configured to use FTIR-ATR spectroscopy techniques when scanning a sample of interest. In more particular aspects, such a method either (a) undertakes a process for determining the acceptability of a pre-existing reference spectrum or a modified reference spectrum before acquiring one or more scans of the sample or (b) undertakes a similar process for determining the acceptability of a pre-existing reference spectrum after first acquiring the one or more scans of the sample.

As described further herein, for either process for determining the acceptability of the pre-existing reference spectrum, such a methodology or applications program logic are particularly suitable for resolving or compensating for a wide range of non-conformities. More particularly, such methods and applications programs of the present invention can compensate for identified non-conformities between the acquired One Scan and the pre-existing reference spectrum and deal with other concerns or issues that the non-conformities indicate could occur while acquiring spectral data during the sample scan process. Such methods and applications program also are suitable for evaluating and assessing the cleanliness of the ATR interface before a sample is coupled to or mounted upon the interface.

Reference shall be made to the foregoing discussion regarding the methodology illustrated in FIG. 1A for those steps having common reference numerals except as otherwise described hereinafter. More specifically, reference should be made to the discussion regarding steps 200, 210, 212 216, 220, 230-238, 240 and 250 of FIG. 1A unless otherwise provided below.

Although the method is illustrated when undertaking a process for determining the acceptability of a pre-existing reference spectrum or a modified reference spectrum before acquiring one or more scans of the sample, this shall not be limiting because as further described herein, such methodologies can be easily adapted so as to undertake a similar process for determining the acceptability of a pre-existing reference spectrum after first acquiring the one or more scans of the sample, which is described further herein.

Such resolving or compensating can include adjusting the pre-existing reference spectrum to compensate for the identified non-conformities. In exemplary embodiments, such a process is described further in connection with the discussion for FIG. 4. Such non-conformities also might identify a concern or issue that could arise while acquiring the sample scan which would need to be accounted or compensated for, such as during the analysis phase of the sample scan. In such a case the methodology can further include a process for identifying or determining the appropriate correction factor, algorithm calculation or the like to address the identified issue or concern, and then causing same to be applied as compensation to the sample scan or sample spectrum. In this way, the methods and applications programs of the present invention can compensate for identified non-conformities between the acquired One Scan and the pre-existing reference spectrum as well as for other concerns or issues that the non-conformities indicate could occur while acquiring spectral data during the sample scan process.

As indicated herein (see discussion regarding FIG. 1A), the spectral data acquired from the One Scan is compared to the pre-existing reference spectrum (Step 214), which comparison is performed to determine if there are any nonconformities between the One Scan and the pre-existing reference spectrum (Step 216). As indicated in the discussion regarding FIG. 1A, if there are no non-conformities identified (NO, Step 216), then the process proceeds with acquiring a sample spectrum and analyzing it (Steps 232-238) as described above in FIG. 1A.

If on the other hand, non-conformities are identified (YES, Step 216), the process proceeds with determining if the non-conformities are of the type and nature which make them resolvable or not (Step 318). Thus, the process proceeds with evaluating and resolving or compensating for any identified non-conformities such as described further herein in connection with FIG. 4. If, it is determined that the non-conformities cannot be resolved or compensated for (NO, Step 318) then the process proceeds to the process for collecting or acquiring a new reference spectrum (Step 230).

However, if these non-conformities are of the type which can be resolved or compensated for, this process continues with resolving or compensating for the non-conformities in the appropriate manner. This can include for example, determining if and how the reference spectrum should be adjusted to resolve or compensate for an identified non-conformity as well as how one should make an adjustment or compensation to an acquired sample spectrum.

As described in connection with FIG. 1A, such resolving and compensating can include a determination that the pre-existing reference spectrum should be modified to resolve or compensate for one or more of the non-conformities as well as the way in which to modify the reference spectrum. As noted herein such a process also can determine that the non-conformity is an indication of a concern or issue that is more properly addressed by taking action later in connection with the analysis of the acquired sample spectrum. As further described herein, this process also can determine that the non-conformity is of a nature that no action need be taken to correct or compensate for it (e.g., noise, water absorption within a known absorption wavelength range), in other words, the non-conformity is per se resolvable. Thus, if all of the identified non-conformities requiring action are deemed resolvable (YES, Step 218), then the process proceeds with correcting the reference spectrum—as needed (Step 220) and then proceeds to the process for acquiring a sample spectrum and analyzing it (Steps 232-238). In the case where the resolution or compensation involves the sample spectrum, such resolving or compensating would be addressed during this sample spectrum acquiring and analysis phase of the process.

As indicated herein, although a user or operator typically cleans the ATR interface prior to proceeding with the scanning of another sample, it is possible that the ATR interface is not completely or sufficiently cleaned before one begins scanning of the next sample. Thus, the methodology and applications program of this aspect/embodiment of the present invention is further configured and arranged so as to perform a check of the cleanliness of the ATR interface. Thus, if such resolving or compensating determines that all but a given or a given set of non-conformities is/are not resolvable (PARTIAL, Step 318) then the process proceeds with determining if the non-conformity/non-conformities correspond to an indication that the ATR interface is clean or not (Step 350, FIG. 3). Reference hereinafter also should be to FIG. 3.

If such an evaluation of the ATR interface results in a determination that the interface is clean (YES, Step 350) then the remaining identified but unresolved non-conformities are determined not to be related to the cleanliness of the ATR interface and so the process proceeds to acquiring a new reference spectrum (Step 230).

As is known to those skilled in the art, certain spectral artifacts appearing in the One Scan can be an indication that the ATR interface is not clean or dirty. If on the other hand it is determined that the remaining unresolved non-conformities are an indication that the interface is not clean (NO, Step 350), then the process proceeds with determining if this is the first time the cleanliness of the ATR interface is being questioned for a given sample scanning process (Step 352). If this is the first time the cleanliness of the ATR interface is being questioned (YES, Step 352) then the process proceeds with cleaning the ATR interface (Step 354). More particularly, the user or operator is instructed to clean the interface. For example, a message is displayed on the measurement device instructing the user or operator to clean the ATR interface or to undertake the ATR interface cleaning process. The user or operator then takes the appropriate actions as are known in the art to clean the interface. Thereafter, the process returns to Step 212 to acquire another One Scan with the cleaned interface.

The methodology can embody further actions to build in a delay between when the user/operator is instructed to clean the interface and when another One Scan is acquired with the cleaned interface. For example, the process could be arranged to display a button, key or the like on the measurement device display for the user to depress or actuate when the cleaning of the interface is complete. Upon depressing the button, key or the like, the process would automatically continue to acquiring the One Scan.

After acquiring a new One Scan with the cleaned interface, the processes as set forth in Steps 214, 216 and 318 is/are repeated to determine if there are any unresolved non-conformities including non-conformities relating to the ATR interface. If the unresolved non-conformities appear to relate to the cleanliness of the ATR interface, the process proceeds to repeating steps 350 and 352. If the process determines again that the ATR interface is dirty, this should be the second time ATR interface cleanliness is being questioned (NO, Step 352) then the process would proceed to obtaining another reference spectrum (Step 230).

As indicated above, reference should be made to the discussion for FIG. 1A as to how the methodology would otherwise proceed from Step 318 in particular as well as the other processes set forth in FIG. 2A not described herein.

Figure 2B:
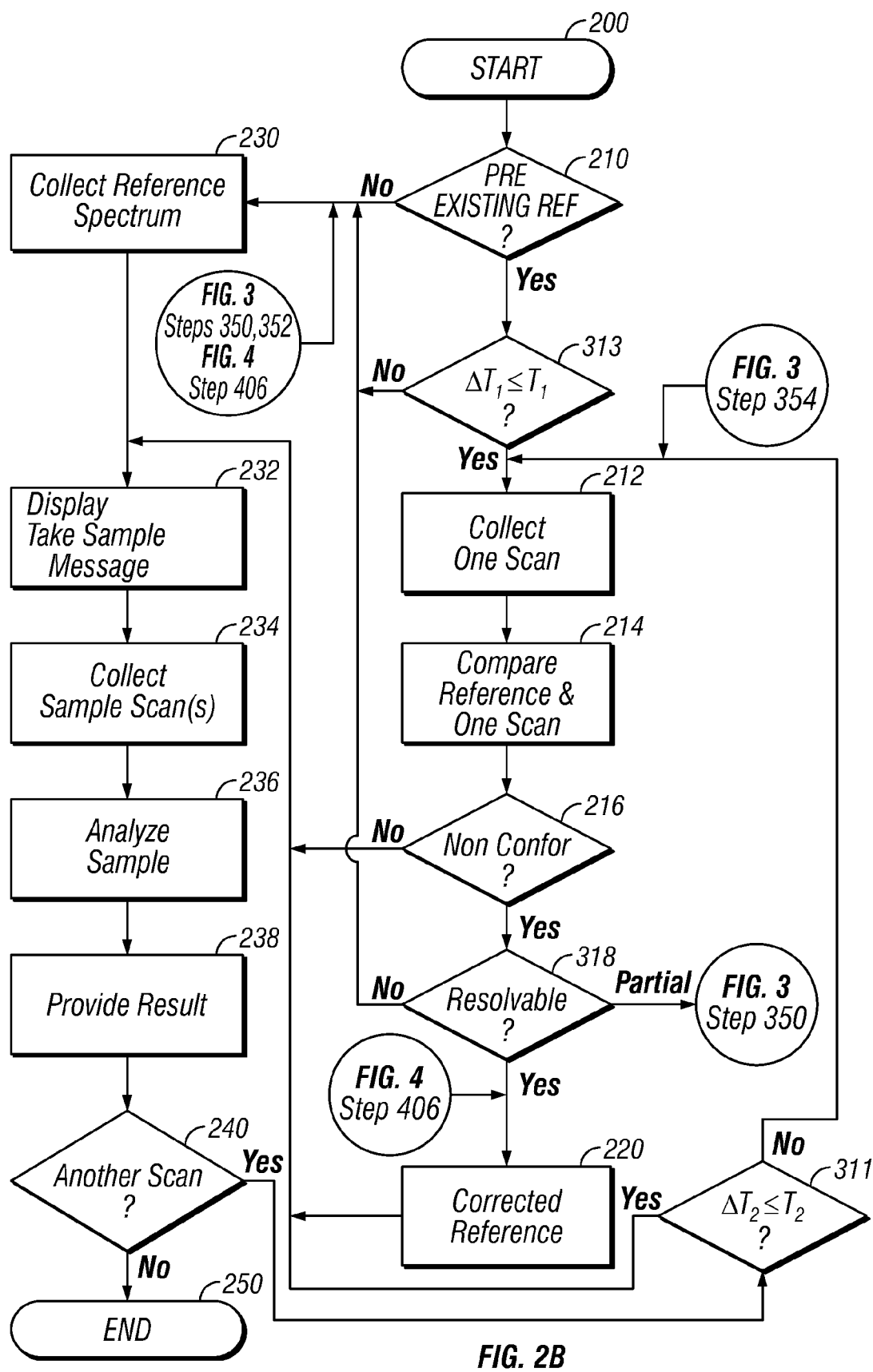
FIG. 2B is a high level flow diagram/flow chart illustrating another methodology or applications program logic according to another aspect or embodiment of the present invention and for use with FTIR-ATR spectroscopy techniques.

Referring now to FIG. 2B, there is shown another high level flow diagram or flow chart illustrating another methodology or applications program logic according to another aspect or embodiment of the present invention. More specifically and as further described herein, such a methodology or applications program logic is particularly suitable for use in connection with measurement devices, apparatuses or systems configured for carrying out FTIR-ATR spectroscopy techniques when scanning a sample of interest. In more particular aspects, such a method either (a) undertakes a process for determining the acceptability of a pre-existing reference spectrum or a modified reference spectrum before acquiring one or more scans of the sample or (b) undertakes a similar process for determining the acceptability of a pre-existing reference spectrum after first acquiring the one or more scans of the sample.

As described further herein, for either process for determining the acceptability of the pre-existing reference spectrum, such a methodology or applications program logic is particularly suitable for resolving or compensating for a wide range of non-conformities between an initial reference or background scan (i.e., One Scan) and a pre-existing reference spectrum. As indicated herein, the methods and applications programs of the present invention can compensate for identified non-conformities between the acquired One Scan and the pre-existing reference spectrum as well as for other concerns or issues that the non-conformities indicate could occur while acquiring spectral data during the sample scan process. Also, such a methodology or applications program logic is particularly suitable for controlling (e.g., re-directing) the process flow in cases where it is possible that the pre-existing reference spectrum has become un-useable.

Reference shall be made to the foregoing discussion regarding the methodology illustrated in FIGS. 1A, 1B and 2A for those steps having common reference numerals except as otherwise described hereinafter. Although the method is illustrated when undertaking a process for determining the acceptability of a pre-existing reference spectrum or a modified reference spectrum before acquiring one or more scans of the sample, this shall not be limiting because as further described herein, such methodologies can be easily adapted so as to undertake a similar process for determining the acceptability of a pre-existing reference spectrum after first acquiring the one or more scans of the sample, which is described further herein.

As indicated herein, there can be circumstances or cases where it would be desirable to bypass the logic process of the methodology or applications program as shown in FIG. 2A so that the process follows another particular given logic pathway. The aspect/embodiment of the methodology or applications logic illustrated in FIG. 2B includes checks to determine if the pre-existing reference spectrum has become un-useable (e.g., as being stale or old) because of the passage of time or if the scanning process has been underway for a sufficient amount of time that would warrant re-checking the acceptability of the pre-existing spectrum or a modified pre-existing spectrum for continued use.

In this regard, after determining that there is a pre-existing reference spectrum available (YES, Step 210), the process proceeds with determining if the time that has elapsed ($\Delta T_1$) since the pre-existing reference spectrum was first saved or stored in the measurement device is less than or equal to a predetermined time—$T_1$, (Step 313). In particular embodiments, the pre-determined time is established so that a spectrum that has been stored for more than $T_1$ is considered to be unacceptable for continued use. In other words, it is believed that conditions have changed, or would have changed, sufficiently since the stored pre-existing spectrum was acquired and/or which would make the spectrum suspect as being stale or un-useable. In this way, action to re-direct the process flow can be automatically implemented without having the user or operator intervene. Also this would avoid the need to go through that part of the methodology necessary to determine that the pre-existing reference spectrum is not acceptable for continued use and then to re-direct the process so as to acquire a new reference spectrum.

If it is determined that the elapsed time is less than or equal to the predetermined time—$T_1$ (YES, Step 313) then the pre-existing reference spectrum is thereafter evaluated to determine if it is acceptable for continued use as described above in connection with FIG. 1A. In such a case, the process proceeds to acquiring the One Scan (Step 212). If it is determined that the elapsed time is greater than the predetermined time (NO, Step 313), then the process proceeds to Step 230 (FIG. 2A) and a new reference spectrum is obtained. In alternative embodiments, if it is determined that the elapsed time is less than the predetermined time—$T_1$ (YES, Step 313) then the pre-existing reference spectrum is thereafter evaluated to determine if it is acceptable for continued use and if it is determined that the elapsed time is equal to or greater than the predetermined time (NO, Step 313), then the process proceeds to Step 230 (FIG. 2A) and a new reference spectrum is obtained.

As indicated herein, the present methodology also includes a check to determine if the scanning process has been underway for a sufficient amount of time that would warrant re-checking the reference spectrum's acceptability for further use. More particularly, a determination is made to determine if the time that has elapsed ($\Delta T_2$) since scanning first began or the elapsed time since the last scan is less than or equal to a predetermined time—$T_2$, (Step 311). The pre-determined time is established so that if the scanning process has continued for more than a desired period of time, the pre-existing spectrum should be checked or re-checked to see if it should be replaced or if it is still considered acceptable for continued use. If it is determined that the elapsed time is less than or equal to the predetermined time (YES, Step 311), then the process proceeds to Step 232 (FIG. 1A) and continues with the acquisition of a spectrum of the sample of interest and an analysis of such a spectrum (Steps 232-238). If it is determined that the elapsed time is greater than the predetermined time (NO, Step 311), then the process proceeds to Step 212 and continues with the process for determining the acceptability of the pre-existing reference spectrum for continued use. This can also include a check as to the cleanliness of the ATR interface.

Figure 4:
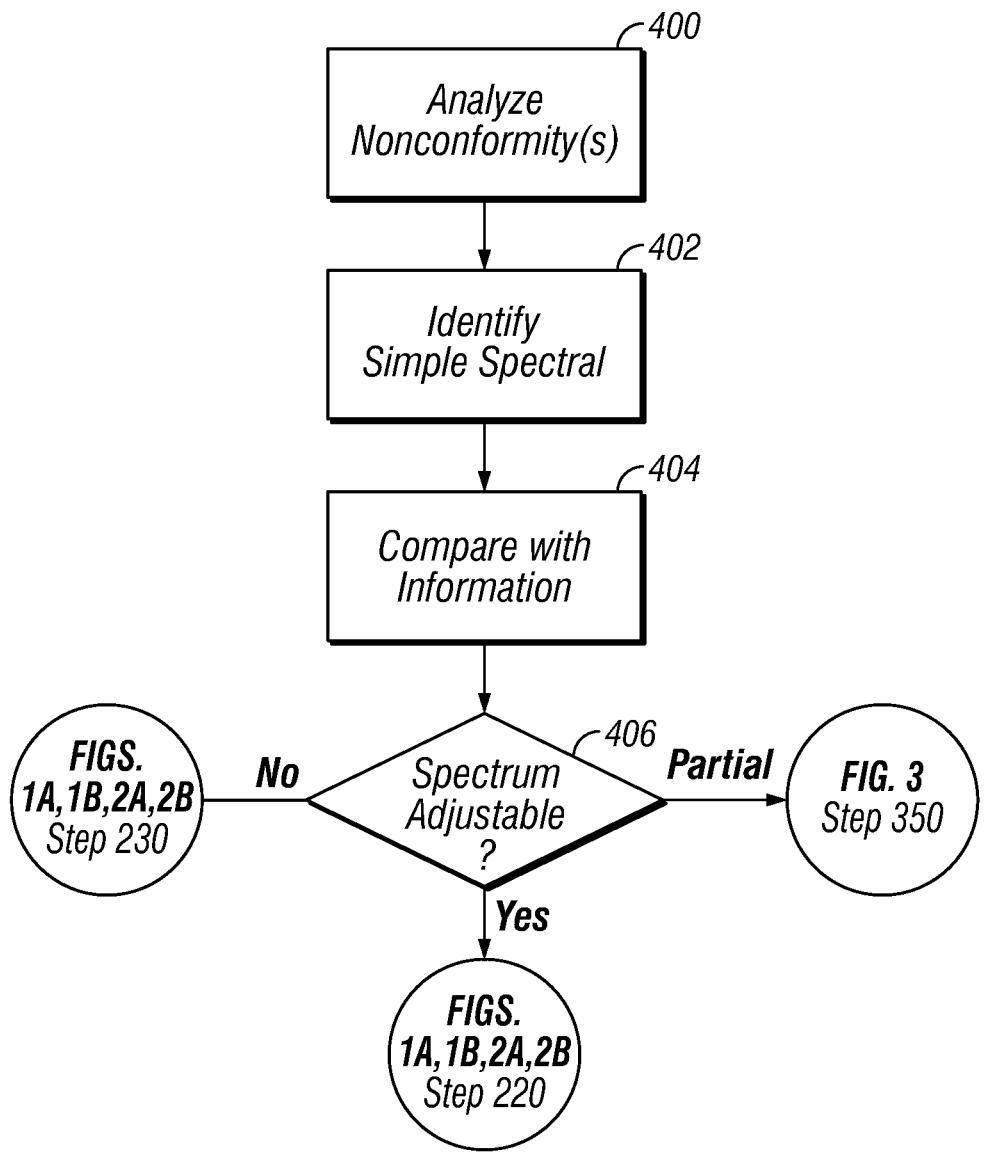
FIG. 4 is a high level flow diagram/flow chart illustrating a process for determining if an identified non-conformity between the taken One Scan and the pre-existing background or reference spectrum is resolvable.

Referring now to FIG. 4 there is shown a high level flow diagram or flow chart illustrating one process for determining if an identified non-conformity/non-conformities between the taken One Scan and the pre-existing background or reference spectrum is/are resolvable. More particularly, the illustrated process is exemplary of the kind of process that would be carried out in Step 218 (FIGS. 1A, B) and the process carried out in Step 318 (FIGS. 2A, B) for determining if the identified non-conformities are resolvable or can be compensated for by the methodology or applications program of the present invention. Reference also should be made to the discussion regarding FIGS. 1A, 1B, 2A and 2B for details of aspects/embodiments of the present invention not otherwise discussed in the following.

Figure 3:
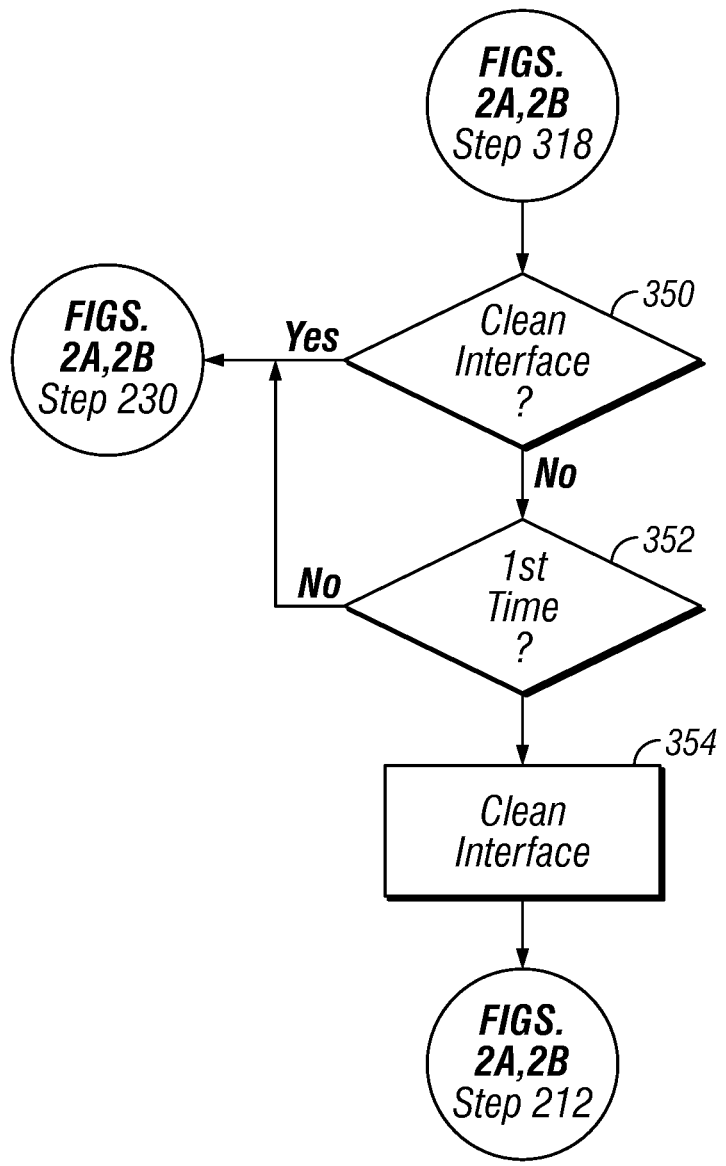
FIG. 3 is a high level flow diagram/flow chart illustrating a process for determining if an ATR interface is clean and follow-on action(s) when it is determined that the interface is not clean.

As indicate above, step 318 differs from step 218 in that in step 318 the resolving process also includes determining if the non-conformities are suggestive of a dirty ATR interface and re-directing the process to the process shown in FIG. 3 to address this concern. Thus and for completeness, FIG. 4 includes the logic steps to reflect an appropriate interconnection with FIG. 3. It should be understood, however, that these interconnections are provided in the case where the measurement device is to be operated so as to perform a FTIR-ATR spectroscopy technique. However and as illustrated in FIGS. 1A, 1B, such an interconnection and related processes can be dispensed with when the measurement device is configured and being operated to perform an FTIR spectroscopy technique.

More particularly and with reference also to FIG. 4, if one or more non-conformities are identified (YES, Step 216), then the process proceeds with analyzing the one or more non-conformities (Step 400) to determine if they are of the type and nature that are resolvable or can be compensated for.

In exemplary embodiments, such a process for evaluating the resultant spectrum to identify non-conformities can include a process for determining or providing a resultant absorption spectrum, which is an absorption spectrum (AB) that results from the conversion of a ratio'ing of the One Scan (B1) to the stored pre-existing reference scan/spectrum (B) such as by using the following relation.

$$AB = -\log 10(B1/B)$$

Arriving at a determination as to whether an identified non-conformity or group of such non-conformities are of the type and nature that are resolvable or can be compensated for typically involves a number of different considerations in such an analysis as well as considering or referring in the analysis to a number of different sources of information such as spectral shapes that can be associated with particular concerns or degradations of a measurement device. An example of this would include a change in sensitivity as a function of wavelength attributable to a change in alignment of the FTIR interferometer. Such a change in alignment might be attributable to thermal expansion or contraction of mechanical elements within the engine due to environmental temperature change. Such a change in sensitivity versus wavelength might be linear in wavelength or quadratic or some other function. Another example would include a change in the shape of the reference spectrum attributable to aging of the infrared source element, or attributable to a temperature change in the infrared source element.

Such an analysis can further proceed with an analysis to determine if any of the one or more non-conformities corresponds to what is referred to as a simple spectral shape or artifact (Step 402). More particularly, such an analysis continues with a computation of the absorbance at each element in the spectrum and then processing the absorbance spectrum along with an uncertainty to identify simple spectral artifacts such as those associated with noise or water absorption within a known absorption wavelength range. This analysis is performed with the view or purpose of removing such simple spectral artifacts from further consideration in terms of adjusting the pre-existing spectrum or for other concerns. Because these simple spectral shapes/artifacts lie within a given uncertainty, they are considered to be indicative of a spectral non-conformity that does not require further action or correction. In other words, the simple spectral shapes are considered to be per se resolvable.

After identifying and eliminating the simple spectral shapes from further consideration, the process proceeds with analyzing and addressing the action to take as to the remaining identified one or more non-conformities. More particularly, the analysis proceeds with comparing the remaining one or more identified non-conformities with other stored information that can be used to evaluate a given non-conformity to determine what action if any should be taken (Step 404). It also is within the scope of the present invention for such a process to include making in-process changes to the pre-existing spectrum based on the determined action except in the case of the simple spectral shapes. As indicated above, in the case of the simple spectral shapes the non-conformity/non-conformities falling into this category are ignored and the pre-existing spectrum is not changed.

More particularly, the analysis proceeds with a comparison of the resultant spectrum or the fitting (AB_FIT) of the resultant spectrum with pre-existing spectral shapes such as those which are stored in the measurement device and available to the digital processor carrying out the methodology of the present invention. Such spectral shapes are provided to remove unwanted time variations that are not accounted for in the pre-existing reference spectrum. These shapes can be those associated with the absorption spectrum of water vapor or they can be empirical spectral shapes derived from a data collection on the measurement device or instrument at a previous time such as for example during calibration at the factory.

Such information also can include design or calibration type information such as the IR spectral output of the lamp, LED or the like being used to illuminate the sample. Such information also can include any time wise variations as to the intensity of the spectral output. For example, the output intensity could have varied from whence the pre-existing reference spectrum was acquired and when the One Scan was acquired.

Thereafter the process could continue with computing a residual spectrum: AB-AB_FIT. Thereafter the process can continue with another computing, in small wavenumber chunks, of the likelihood that the residual is within the uncertainty of the measurement by chance. This can be referred to as a LOCAL_LIKELIHOOD. This is usually a fractional number between zero (0) and 1.

If any of the LOCAL_LIKLIHOOD values are below a threshold value, then the pre-existing reference spectrum is determined to be not okay for continued use, that the interface is dirty or both. If any of the LOCAL_LIKLIHOOD values in wavenumber regions other than those known to be associated with instrument or environment variation are below a threshold, then the interface or the crystal of such an interface is considered to be dirty. In the case where the interface is determined to be dirty or unclean or is suggestive of a dirty interface, such a determination can be used in Step 406 (PARTIAL, Step 406) to redirect the process to step 350 of FIG. 3 and not to proceed to Step 230 (FIGS. 1A, 1B, 2A, 2B) as well as not proceeding to Step 220 (FIGS. 1A, 1B, 2A, 2B). The process thereafter follows the logic of FIG. 3 and to the appropriate interconnections back to FIG. 1A, 1B, 2A, or 2B. As indicated in these figures, after the interface is cleaned the resolving or compensating process is repeated using a new One Scan for the cleaned interface. It should be noted that the logic of FIG. 3 is not provided herein in this discussion for convenience.

From the foregoing process, it can be seen that, in the analysis phase, determinations are made to identify simple spectral artifacts that should be basically ignored as well as to determine or identify spectral artifacts relating to other non-conformities that are resolvable such as by removing them from, or compensating for them, in the residual spectrum. If these spectral artifacts cannot be removed or the LOCAL-_LIKELIHOOD analysis indicates that the pre-existing reference spectrum cannot be used, then the process proceeds to Step 230 as herein described and a new reference spectrum is obtained. As indicated herein, after acquiring such a new reference spectrum, the process continues with the acquisition of a spectrum of the sample of interest and the performance of an analysis of such a spectrum (Steps 232-238).

If it is determined from the analysis phase that the spectral artifacts can be either resolved or compensated for removed by modifying the pre-existing reference spectrum (YES, Step 406), then the process proceeds to Step 220 (FIGS. 1A, 1B, 2A, 2B), and the pre-existing or prior reference spectrum is adjusted (Step 220). It also should be recognized that it is contemplated that such modification of the pre-existing spectrum can occur at different timings during the above-described process, and that an in-process modified reference spectrum be created. However, this in-process modified reference spectrum does not replace the pre-existing reference spectrum until it is determined that modified reference spectrum resolves the identified one or more non-conformities. If yes, then the process saves the modified reference spectrum and thereafter, the process proceeds to Step 232 (FIGS. 1A, 1B, 2A, 2B) and continues with the acquisition of a spectrum of the sample of interest and an analysis of such a spectrum (Steps 232-238, FIGS. 1A, 1B, 2A, 2B). The modified reference spectrum thereafter becomes the pre-existing reference spectrum.

In this regard, appropriate indications/instructions are saved in the event the analysis also identifies other concerns that could occur when acquiring the sample scan(s) and which should be compensated for in accordance with the identified information/compensating instructions. In such a case, these instructions are saved and implemented during the analysis phase of the acquisition and analysis steps associated with the sample scan process (Steps 232-238).

If it is determined that adjustment of the reference spectrum is not possible or is not likely to succeed in resolving the one or more non-conformities remaining after the identification of simple spectral artifacts or the like (NO, Step 406), then the process proceeds to Step 230 and acquiring a new reference spectrum.

While the above described aspects/embodiments of the present invention are directed to applications involving FTIR spectroscopy or FTIR-ATR spectroscopy techniques, as indicated hereinabove, this is not limiting as it is within the scope of the present invention for the methodology of the present invention to be adapted for use with other spectroscopic techniques. Such other spectroscopic techniques include, but are not limited to Diffuse reflectance spectroscopy, Hadamard spectroscopy, fluorescence spectroscopy, and ellipsometry. More specifically, such other spectroscopic techniques can be adapted to use any of the methods described hereinabove (e.g., such as in connection with FIGS. 1-4) and the devices or apparatuses implementing such other spectroscopic techniques also can be configured so as to embody applications programs that can perform the above described functions.

In more particular aspects/embodiments, such other spectroscopic techniques are adapted or modified so as to include method steps for establishing the acceptability to continue to use a pre-existing reference spectrum that is available for use with such other spectroscopic techniques as well as a methodology for determining how to modify such a pre-existing reference spectrum for continued use or under what conditions one should acquire another reference spectrum. Such methods or methods steps include the processes or method steps as illustrated and discussed above in connection with FIGS. 1-4.

Such a process also is such as to allow other aspects of these other spectroscopic techniques, such as when and how to acquire scans and a spectrum of a sample of interest, to be performed in a manner consistent with these other techniques. As also indicated herein, such methods of the present invention also are such as to allow the methods of the present invention to be carried out either before or after acquiring such sample scans of the sample of interest.

In more particular aspects/embodiments, such other spectroscopic techniques are adapted or modified so as to either undertake a process for determining the acceptability of a pre-existing reference spectrum before acquiring one or more scans of the sample or undertake a similar process for determining the acceptability of a pre-existing reference spectrum after first acquiring the one or more scans of the sample. As described further herein, either process for determining the acceptability of the pre-existing reference spectrum also includes resolving any spectral non-conformities with the pre-existing reference spectrum identified during such a process as herein further described. Such a process includes the method steps described above in connection with FIGS. 1-4.

In more particular aspects, such a method is directed to reducing frequency of taking background or reference spectra when using such spectroscopic techniques. More particularly, such a method either (a) undertakes a process for determining the acceptability of a pre-existing reference spectrum before acquiring one or more scans of the sample or (b) undertakes a process in which the one or more scans of the sample are acquired first and then continues with performing a similar process for determining the acceptability of a pre-existing reference spectrum. As described further herein, either process for determining the acceptability of the pre-existing reference spectrum also includes resolving any spectral non-conformities with the pre-existing reference spectrum identified during such a process. As indicated herein reference shall be made to the discussion regarding FIGS. 1-4 for the related method steps and processes.

As also indicated above in the discussions regarding FIGS. 1B, 2B, and 3-4, such methods also are such as to allow one to establish the cleanliness of an ATR interface for those other spectroscopic techniques which embody an ATR interface.

As indicated hereinabove, the methods of the present invention are such that such a method either (a) undertakes a process for determining the acceptability of a pre-existing reference spectrum or a modified reference spectrum before acquiring one or more scans of the sample or (b) undertakes a similar process for determining the acceptability of a pre-existing reference spectrum after first acquiring the one or more scans of the sample. As described further herein, either process for determining the acceptability of the pre-existing reference spectrum also includes resolving any spectral non-conformities with the pre-existing reference spectrum identified during such a process as herein further described. In the discussion herein reference to determining the acceptability of a pre-existing reference spectrum shall be understood to include determining the acceptability of a pre-existing reference spectrum that has been modified (i.e., modified pre-existing spectrum or modified reference spectrum) using the methodology of the present invention.

As to the undertaking of a similar process for determining the acceptability of a pre-existing reference spectrum after first acquiring the one or more scans of the sample, it is within the skill of those knowledgeable in the relevant arts based on the figures and discussion herein, to modify the present methodology in a manner that allows the scans of the sample to be undertaken in advance of determining the acceptability of the pre-existing spectrum. Typically, regardless of when the sample is scanned, the analysis of the sample scans will generally follow the processes of the present invention for determining the acceptability of the pre-existing reference spectrum as well as any modifications thereto.

In its broadest aspects/embodiments, the method steps 232 and 234 as illustrated in the methods shown in FIGS. 1-2 can be located so as to be performed before step 200, after step 200 and before step 210 or after step 210 and before the next illustrated method step. In such cases, the processes that are shown as being directed to step 232 also would be re-directed to method step 234.

In one particular embodiment, steps 232 and 234 are arranged so as to follow step 210, so that sample scanning is not performed unless there is a pre-existing reference spectrum available before sample scanning. In the case where in step 210 it is determined that there is no pre-existing reference spectrum (No, Step 210) or that the pre-existing reference spectrum is stale in Step 313 (FIG. 1B, 2B), then the process would proceed with acquiring a reference spectrum (Step 230) and then reverting to the sample scanning processes.

While the foregoing is illustrative, it should be recognized that it is within the scope of the present invention for the sample scanning processes (e.g., steps 232, 234) to be arranged so as to occur at other places in the methodology or method steps illustrated in FIG. 1-4.

As indicated herein, according to yet further aspects/embodiments, the present invention also features a computer readable storage medium on which is stored an applications program including instructions, criteria and/or code segments for carrying out the steps of the methods as herein described and embodied in such applications programs.

Figure 5:
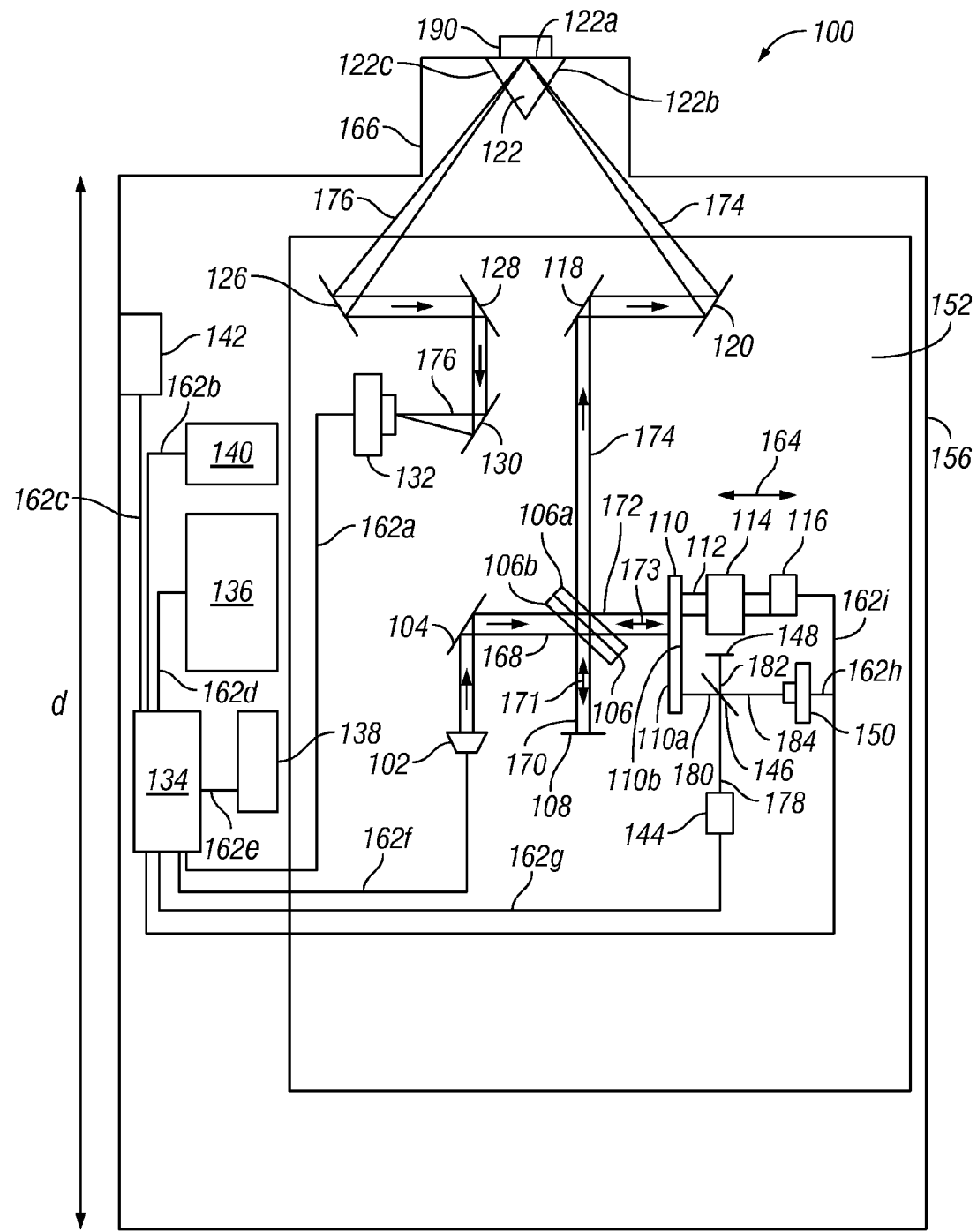
FIG. 5 is a block diagram or schematic diagram of an exemplary measurement device that is configurable with a method or applications program of the present invention.

As also indicated herein, the above described methods and related applications programs of the present invention are particularly suitable for adaptation and use with any of a number of measurement devices as are known to those skilled in the art. In particular, measurement devices embodying a processor, microprocessor, digital processor or logic circuits (e.g., ASIC, PGA) as are known to those skilled in the art which control the process for the detection and processing of signals. Referring now to FIG. 5 there is shown a block diagram or schematic diagram of an exemplary measurement device such as that more particularly described in U.S. Pat. No. 8,248,588, the teachings of which are incorporated by reference. Such a measurement device also is configurable so as to embody a method or applications program of the present invention. In this regard, reference shall be made to this patent for further details aspects and embodiments of such a measurement device not expressly provided herein.

There is shown in FIG. 5, a schematic diagram of a measurement device 100. Such a device 100 includes an optical assembly mounted on an assembly support 152 that is fixed within an enclosure 156. The optical assembly includes: radiation sources 102 and 144; mirrors 104, 108, 110, 148, 118, 120, 126, 128, and 130; beam-splitters 106 and 146; detectors 132 and 150; and prism 122. The device 100 also includes a shaft 112, a bushing 114, and an actuator 116 coupled to mirror 110, and an electronic processor 134, an electronic display 136 (e.g., including a flat panel display element such as a liquid crystal display element, an organic light-emitting diode display element, an electrophoretic display element, or another type of display element), an input device 138, a storage unit 140, and a communication interface 142. The electronic processor 134 is in electrical communication with detector 132, storage unit 140, communication interface 142, display 136, input device 138, radiation sources 102 and 144, detector 150, and actuator 116, respectively, via communication lines 162a-i.

The measurement device 100 is configured for use as a Fourier transform infrared (FTIR) spectrometer. More particularly, such a measurement device is further configured so as to embody an ATR interface. During operation, the radiation 168 is generated by radiation source 102 under the control of processor 134. The radiation 168 is directed by mirror 104 to be incident on beam splitter 106, which is formed from a beam splitting optical element 106a and a phase compensating plate 106b, and which divides radiation 168 into two beams. A first beam 170 reflects from a surface of beam splitter 106, propagates along a beam path which is parallel to arrow 171, and is incident on fixed mirror 108. The fixed mirror 108 reflects first beam 170 so that first beam 170 propagates along the same beam path, but in an opposite direction (e.g., towards beam splitter 106).

A second beam 172 is transmitted through beam splitter 106 and propagates along a beam path which is parallel to arrow 173. The second beam 172 is incident on a first surface 110a of movable mirror 110. The movable mirror 110 reflects the second beam 172 so that beam 172 propagates along the same beam path, but in an opposite direction (e.g., towards beam splitter 106).

The first and second beams 170 and 172 are combined by beam splitter 106, which spatially overlaps the beams to form incident radiation beam 174. The mirrors 118 and 120 direct incident radiation beam 174 to enter prism 122 through prism surface 122b. Once inside prism 122, radiation beam 174 is incident on surface 122a of the prism 122. The surface 122a of prism 122 is positioned such that it contacts a sample of interest 190. When the radiation beam 174 is incident on the surface 122a, a portion of the radiation is coupled into sample 190 through surface 122a. Typically, for example, sample 190 absorbs a portion of the radiation in radiation beam 174.

The radiation beam 174 undergoes total internal reflection from the surface 122a of the prism 122 as reflected beam 176. The reflected beam 176 includes, for example, the portion of incident radiation beam 174 that is not absorbed by sample 190. The reflected beam 176 leaves prism 122 through surface 122c, and is directed by mirrors 126, 128, and 130 to be incident on detector 132. Under the control of processor 134, the detector 132 measures one or more properties of the reflected radiation in reflected beam 176. For example, detector 132 can determine absorption information about sample 190 based on measurements of the reflected beam 176.

Typically, the radiation in reflected beam 176 is measured at a plurality of positions of movable mirror 110. The mirrors 108 and 110, together with beam splitter 106, are arranged to form a Michelson interferometer, and by translating mirror 110 in a direction parallel to arrow 164 prior each measurement of reflected radiation 176, the plurality of measurements of the radiation in reflected beam 176 form an interferogram. The interferogram includes information such as sample absorption information. The processor 134 can be configured to apply one or more mathematical transformations to the interferogram to obtain the sample absorption information. For example, processor 134 can be configured to transform the interferogram measurements from a first domain (such as time or a spatial dimension) to a second domain (such as frequency) that is conjugate to the first domain. The transform (s) that is/are applied to the data can include a Fourier transform, for example.

The movable mirror 110 is coupled to the shaft 112, bushing 114, and actuator 116. The shaft 112 moves freely within bushing 114, and a viscous fluid is disposed between shaft 112 and bushing 114 to permit relative motion between the two. The mirror 110 moves when the actuator 116 receives control signals from processor 134 via communication line 162i. The actuator 116 initiates movement of the shaft 112 in a direction parallel to arrow 164, and mirror 110 moves in concert with shaft 112. The bushing 114 provides support for shaft 112, preventing wobble of shaft 112 during translation. However, the bushing 114 and shaft 112 are effectively mechanically decoupled from one another by the fluid disposed between them; mechanical disturbances such as vibrations are coupled poorly between shaft 112 and bushing 114. As a result, the alignment of the Michelson interferometer remains relatively undisturbed even when mechanical perturbations such as vibrations are present in other portions of device 100.

To measure the position of mirror 110, device 100 includes a second interferometer assembly that includes a radiation source 144, beam splitter 146, mirror 148, and detector 150. These components are arranged to form a Michelson interferometer. During a mirror position measurement operation, radiation source 144 receives a control signal from processor 134 via communication line 162g, and generates a radiation beam 178. The beam 178 is incident on beam splitter 146, which separates radiation beam 178 into a first beam 180 and a second beam 182. The first beam 180 reflects from the surface of beam splitter 146 and is incident on a second surface 110b of mirror 110. The second surface 110b is positioned opposite first surface 110a of mirror 110. The first beam 180 reflects from surface 110b and returns to beam splitter 146.

The second beam 182 is transmitted through beam splitter 146, reflected by mirror 148, and returned to beam splitter 146. The beam splitter 146 combines (e.g., spatially overlaps) reflected beams 180 and 182, and the combined beam 184 is directed to detector 150. Detector 150 receives control signals from processor 134 via communication line 162h, and is configured to measure an intensity of combined beam 184. As the position of mirror 110 changes (e.g., due to translation of mirror 110 along a direction parallel to arrow 164), the intensity of the radiation measured by detector 150 changes due to interference between first beam 180 and second beam 182 in combined beam 184. By analyzing the changes in measured radiation intensity from detector 150, processor 134 can determine with high accuracy the position of mirror 110.

Position information for mirror 110 is combined by processor 134 with measurements of the radiation in reflected beam 176 to construct an interferogram for sample 190. As discussed above, processor 134 can be configured to apply a Fourier transform to the interferogram to obtain absorption information about sample 190 from the interferogram. The absorption information can be compared by processor 134 to reference information (e.g., reference absorption information) stored in storage unit 140 to determine an identity of sample 190. For example, the processor 134 can determine whether the absorption information for the sample matches any one or more of a plurality of sets of reference absorption information for a variety of substances that are stored as database records in storage unit 140. If a match is found (e.g., the sample absorption information and the reference information for a particular substance agree sufficiently), then sample 190 is considered to be identified by processor 134. The processor 134 can send an electronic signal to display 136 along communication line 162d that indicates to a system operator that identification of sample 190 was successful, and provides the name of the identified substance. The signal can also indicate to the system operator how closely the sample absorption information and the reference information agree. For example, numeric values of one or more metrics can be provided which indicate the extent of correspondence between the sample absorption information and the reference information on a numerical scale.

If a match between the sample absorption information and the reference information is not found by the processor 134, the processor can send an electronic signal to the display 136 that indicates to the system operator that sample 190 was not successfully identified. The electronic signal can include, in some embodiments, a prompt to the system operator to repeat the sample absorption measurements.

The processor 134 also can be configured so that any application program according to the present invention is loaded into the processor for execution thereon. Thus the measurement device 100 can determine the acceptability of a pre-existing reference spectrum, also stored on the measurement device, for continued use in the process for identifying a sample of interest.

Reference information stored in storage unit 140 can include reference absorption information for a variety of different substances, as discussed above. The reference information can also include one or more lists of prohibited substances. Lists of prohibited substances can include, for example, substances that passengers on commercial airline flights are not allowed to carry. Lists of prohibited substances can also include, for example, substances that are not permitted in various public locations such as government buildings for security and public safety reasons. If identification of the sample 190 is successful, the processor 134 can be configured to compare the identity of the sample 190 against one or more lists of prohibited substances stored in storage unit 140. If the sample 190 appears on a list as a prohibited substance, the processor 134 can alert the system operator that a prohibited substance has been detected. The alert can include a warning message displayed on display 136 and/or a colored region (e.g., a red-colored region) on display 136. The processor 134 also can be configured to sound an audio alarm via a speaker to alert the system operator.

The storage unit 140 typically includes a re-writable persistent flash memory module. The memory module, which is removable from enclosure 156, is configured to store a database that includes a library of infrared absorption information about various substances. The processor 134 can retrieve reference absorption information from storage unit 140 via a request transmitted on communication line 162b. The storage unit 140 can also store device settings and other configuration information such as default operating parameters. As indicated herein, the storage unit also can store a pre-existing reference spectrum and other information that is used during the assessment of the acceptability of the pre-existing reference spectrum for use in subsequently acquired scans of a sample of interest. Other storage media can also be included in storage unit 140, including various types of re-writable and non-rewritable magnetic media, optical media, and electronic memory.

The measurement device 100 also includes a communication interface 142, which receives and transmits signals from/to processor 134 via communication line 162c. The communication interface 142 includes a wireless transmitter/receiver unit that is configured to transmit signals from processor 134 to other devices, and to receive signals from other devices and communicate the received signals to processor 134. Typically, for example, the communication interface 142 permits the processor 134 to communicate with other devices—including other measurement devices 100 and/or computer systems—via a wireless network that includes multiple devices connected to the network, and/or via a direct connection to another device. The processor 134 can establish a secure connection (e.g., an encrypted connection) to one or more devices to ensure that signals can only be transmitted and received by devices that are approved for use on the network.

The processor 134 communicates with a central computer system to update the database of reference information stored in storage unit 140. The processor 134 is configured to periodically contact the central computer system to receive updated reference information, and processor 134 can also receive automatic updates that are delivered by the central computer system. The updated reference information can include reference absorption information, for example, and can also include one or more new or updated lists of prohibited substances. Such updated information also can include updates to the information that is used during the assessment of the acceptability of the pre-existing reference spectrum for use in subsequently acquired scans of a sample of interest.

The processor 134 can also communicate with other measurement devices to broadcast alert messages when certain substances—such as substances that appear on a list of prohibited substances—are identified, for example. Alert messages can also be broadcast to one or more central computer systems. Alert information—including the identity of the substance, the location at which the substance was identified, the quantity of the substance, and other information—can also be recorded and broadcast to other measurement devices and computer systems.

In some embodiments, measurement device 100 can be connected to other devices over other types of networks, including isolated local area networks and/or cellular telephone networks. The connection can be a wireless connection or a wired connection. Signals, including alert messages, can be transmitted from processor 134 to a variety of devices such as cellular telephones and other network-enabled devices that can alert personnel in the event that particular substances (e.g., prohibited substances) are detected by measurement device 100.

Typically, the input device 138 includes a control panel that enables a system operator to set configuration options and change operating parameters of measurement device 100. In some embodiments, measurement device 100 can also include an internet-based configuration interface that enables remote adjustment of configuration options and operating parameters. The interface can be accessible via a web browser, for example, over a secured or insecure network connection. The internet-based configuration interface permits remote updating of measurement device 100 by a central computer system or another device, ensuring that all measurement devices that are operated in a particular location or for a particular purpose have similar configurations. The internet-based interface can also enable reporting of device configurations to a central computer system, for example, and can enable tracking of the location of one or more measurement devices.

The radiation source 102 includes one or more broadband radiation emitters that is/are configured to provide infrared radiation, so that measurement device 100 functions as an infrared spectrometer. Such broadband emitters include, but are not limited to, heated silicon carbide elements or tungsten filament sources. The wavelength range for emitters of the present invention can span from 2.5 microns to 15.4 microns, and "typical" instruments might span from as short as 1 micron wavelength to as long as 25 microns (common) or even as much as 100 microns or longer (uncommon).

In the case of a plurality of emitters, such a measurement apparatus, for example the processing device, can selectively control operation of the individual emitters so as to provide individual broad bands of radiation that can be composed of different frequencies of radiation.

In certain embodiments, the properties of radiation 168 provides by source 102 can be altered by control signals from processor 134. For example, processor 134 can adjust an intensity and/or a spectral distribution of radiation 168. Processor 134 can adjust spectral properties of radiation 168 by activating one or more filter elements (not shown in FIG. 5), for example. In general, measurement device 100 can include lenses, mirrors, beam splitters, filters, and other optical elements that can be used to condition and adjust properties of radiation 168.

The detector 132 is configured to measure reflected radiation beam 176 after the beam leaves prism 122. Typically, detector 132 includes a pyroelectric detector element that generates an electronic signal, where the magnitude of the electronic signal is proportional to the rate of change of intensity incident on the detector. In general, however, detector 132 can include a variety of other detection elements. For example, in some embodiments, detector 132 can be a photoelectric detector (e.g., a photodiode) that generates an electronic signal with a magnitude that depends on the intensity of radiation beam 176.

The radiation source 144 generates radiation beam 178 that is used to measure the position of mirror 110. Radiation source 144 includes a vertical cavity surface-emitting laser (VCSEL) that generates radiation having a central wavelength of 850 nm. In general, radiation source 144 can include a variety of sources, including laser diodes, light-emitting diodes, and lasers. The radiation beam 178 can have a central wavelength in an ultraviolet region, a visible region, or an infrared region of the electromagnetic spectrum. For example, in some embodiments, a central wavelength of radiation beam 178 is between 400 nm and 1200 nm (e.g., between 400 nm and 500 nm, between 500 nm and 600 nm, between 600 nm and 700 nm, between 700 nm and 800 nm, between 800 nm and 900 nm, between 900 nm and 1000 nm, between 1000 nm and 1100 nm, between 1100 nm and 1200 nm).

The detector 150 can include a variety of different detection elements configured to generate an electronic signal in response to beam 184. In some embodiments, for example, detector 184 includes a photoelectric detector, such as a photodiode. Generally, any detection element that generates an electronic signal that is sensitive to changes in an intensity of beam 184 can be used in detector 150.

As shown in FIG. 5, the mirror 110 includes two opposite reflecting surfaces 110a and 110b. The mirror 110 includes a substrate 110c (formed of glass or fused silica, for example), with a first coating 110d disposed on substrate 110c to form first reflecting surface 110a, and a second coating 110e disposed on an opposite surface of substrate 110c to form second reflecting surface 110e. Typically, beams 172 and 180, which are incident on surfaces 110a and 110b of mirror 110, respectively, have different central wavelengths. The materials that form first coating 110d and second coating 110e are selected to provide high reflectivity for beams 172 and 180. In some embodiments, depending on the central wavelengths of beams 172 and 180, a single coating material with high reflectivity at both central wavelengths is used to form coatings 110d and 110e. In certain embodiments, two different materials are used to form coatings 110d and 110e, where each coating material is selected to provide high reflectivity of beam 172 or beam 180, as appropriate.

The use of two different coating materials—each selected to provide high reflectivity for a beam having a particular central wavelength—provides an advantage over conventional position-measuring interferometer systems. In certain conventional systems, for example, beams 172 and 180 reflect from a common surface of mirror 110 (e.g., surface 110a). If the beams 172 and 180 have central wavelengths that differ appreciably, then it is difficult to find a material for coating 110d that has very high reflectivity for both beams. As a result, one or even both of beams 172 and 180 is reduced in intensity due to reflection losses from mirror 110.

The shaft 112 and bushing 114 permit smooth, vibration-decoupled motion of mirror 110 in a direction parallel to arrow 164 (e.g., in a direction parallel to the optical path of beam 172). In the embodiment shown in FIG. 5, both the shaft 112 and bushing 114 are substantially cylindrical, and bushing 114 has a central bore adapted to receive shaft 112. In general, however, shaft 112 can be replaced by any member that is connected to mirror so that the member moves together with mirror 110. Similarly, bushing 114 can, in general, include any sleeve or other member that is adapted to receive shaft 112, and configured to permit motion of shaft 112 and mirror 110 relative to bushing 114.

The overall translation mechanism that is configured to translate mirror 110 includes shaft 112, bushing 114, and actuator 116. The actuator 116 is coupled to shaft 112 and, on receiving suitable control signals from processor 134, translates mirror 110 in a direction parallel to the optical path of beam 172 by applying a force to shaft 112. Due to the applied force, the shaft 112 moves relative to bushing 114, causing translation of mirror 110. Typically, the actuator 116 includes a coil winding that is configured to generate a magnetic field when a control signal is received. The magnetic field produces an attractive or repulsive force between actuator 116 and bushing 114 (which can be formed from a metal and/or magnetic material, for example), causing translational motion of actuator 116 and coupled shaft 112 relative to bushing 114. In general, many different types of actuators can be used to translate mirror 110. Exemplary alternative actuators include voice coil actuators, stepper motors, flexure-based translation stages, and piezoelectric devices.

The measurement device 100 is generally configured to make multiple measurements of infrared absorption information from sample 190 to construct an interferogram. Typically, for example, each of the multiple measurements corresponds to a different position of mirror 110 along an axis parallel to the beam path of beam 172. In certain embodiments, a maximum difference among the different positions of mirror 110 is 0.5 mm or more (e.g., 1 mm or more, 2 mm or more, 3 mm or more, 4 mm or more, 5 mm or more, 7 mm or more, 10 mm or more).

As discussed above, during operation, the prism 122 is placed in contact with sample 190. The radiation is incident on surface 122a of prism 122 that contacts sample 190, and a portion of the incident radiation couples into sample 190 where it is absorbed. The remaining radiation undergoes total internal reflection from surface 122a of prism 122, and is detected by a suitable detector 132. To contact sample 190, prism 122 is positioned in an aperture than includes a protrusion 166 formed in a wall of enclosure 156. Typically, protrusion 166 includes a liquid-proof seal to prevent sample fluid from entering enclosure 156 when prism 122 contacts a liquid sample 190.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:
1. A method for reducing frequency of taking background spectra when using one of FTIR spectroscopy or FTIR-ATR spectroscopy techniques, said method comprising the steps of:
   determining if there is a pre-existing reference spectrum available;
   acquiring one or more scans of a sample of interest;
   determining one of acceptability of the pre-existing reference spectrum or of a modified pre-existing reference spectrum either (a) before acquiring the one or more scans of the sample or (b) after acquiring the one or more scans of the sample;
   wherein said determining the acceptability of the pre-existing reference spectrum or of the modified pre-existing reference spectrum includes:
   acquiring a present reference scan;
   comparing the present reference scan and the pre-existing reference spectrum to determine if there are any non-conformities there between;
   if one or more non-conformities are found between the present reference scan and the pre-existing reference spectrum, determining if the one or more non-conformities are resolvable or not;
   if the one or more non-conformities are resolvable; resolving each non-conformity in a manner determined to resolve the one or more non-conformities; and
   if the one or more non-conformities are not resolvable, then acquiring a new reference spectrum.

2. The method of claim 1, wherein said resolving further includes evaluating each non-conformity so as to determine if any of the non-conformities corresponds to a simple spectral artifact and not taking any action to correct for such simple spectral artifacts.

3. The method of claim 1, further including storing one or more spectral shapes that are associated with one or more given spectral effects; and wherein said resolving further includes comparing the one or more stored spectral shapes with the identified one or more non-conformities to determine a relationship between a given stored spectral shape and a particular non-conformity; and if a relationship is determined, using the stored spectral shape to determine a corrective action to resolve the non-conformity.

4. The method of claim 1, further comprising storing other spectral information and wherein said resolving includes evaluating each non-conformity with the other spectral information to determine if the other information relates to the non-conformity and the resolution of the non-conformity and if it is determined that the other information relates, then applying a corrective action related to the other information to resolve the non-conformity.

5. The method of claim 1, wherein said determining if the non-conformities are resolvable includes:
   comparing spectrums for each of the present reference scan and the pre-existing reference spectrum to identify the spectral region(s) exhibiting a non-conformity;
   comparing each identified non-conformity with saved spectral information to determine if the non-conformity is one of environment related, instrument related or spectral related;
   determining if the non-conformity with the pre-existing reference spectrum is resolvable by adjusting the pre-existing spectrum based on the saved information and the present reference scan;
   if said determining determines that the pre-existing reference spectrum is resolvable, adjusting the pre-existing reference spectrum.

6. The method of claim 1, wherein the spectroscopy technique embodies an ATR interface and wherein said resolving includes evaluating the one or more non-conformities to determine if one or more non-conformities are indicators of a dirty ATR interface; and if determined as being a dirty interface providing an indication to clean the interface.

7. The method of claim 6, wherein after cleaning of the interface, repeating said steps of acquiring, comparing and determining to determine if the ATR interface is clean.

8. The method of claim 6, wherein after cleaning the interface and repeating said determining if one or more non-conformities are indicators of a dirty ATR interface, determining if this is the first time such a determination is being made, and if it is determined that this is not the first time, causing the process to proceed to acquiring a new reference spectrum.

9. The method of claim 1, wherein:
   before acquiring the one or more scans of the sample, providing a message to a user that instructs the user to take the actions involved with acquiring the sample spectrum; and
   after acquiring the sample spectrum, analyzing the sample scan(s) in conjunction with one of the pre-existing reference spectrum or the modified pre-existing reference spectrum so as to yield a corrected sample spectrum.

10. The method of claim 9, wherein after said analyzing is performed, said method includes providing results of such analyzing to the user.

11. The method of claim 10, wherein said providing includes displaying the results to the user.

12. The method of claim 1, wherein before acquiring a present reference scan and after determining that a pre-existing reference spectrum is available; determining if a predetermined amount of time has elapsed or not since the pre-existing reference spectrum was acquired; if said predetermined amount of time has elapsed then causing the process to proceed to acquiring a new reference spectrum and if said predetermined time has not elapsed then causing the process to proceed with acquiring a present scan and the process that follows for determining the acceptability of the pre-existing reference spectrum or the modified pre-existing reference spectrum.

13. A measurement apparatus for use in one of FTIR spectroscopy and FTIR-ATR spectroscopy of a sample, such a measurement apparatus comprising:
   a means for irradiating the sample;
   a detection device that is configured and arranged to detect radiation emanating from the sample and providing an output of the detected radiation;
   a processing device including a digital processor or microprocessor, which is operably coupled to the detection device for controlling operation of the measurement apparatus including the irradiating means and the detection device and processing the detection device outputs;
   an applications program for execution on the processing device, such an applications program including instructions, criteria and code segments for carrying out a methodology including the steps of:
   determining if there is a pre-existing reference spectrum available;
   acquiring one or more scans of a sample of interest;
   determining one of acceptability of the pre-existing reference spectrum or of a modified pre-existing reference spectrum either (a) before acquiring the one or more scans of the sample or (b) after acquiring the one or more scans of the sample;
   wherein said determining the acceptability of the pre-existing reference or of the modified pre-existing reference spectrum includes:
   acquiring a present reference scan;
   comparing the present reference scan and the pre-existing reference spectrum to determine if there are any non-conformities there between;
   if one or more non-conformities are found between the present reference scan and the pre-existing reference spectrum, determining if the one or more non-conformities are resolvable or not;
   if the one or more non-conformities are resolvable; resolving each non-conformity in a manner determined to resolve the one or more non-conformities; and
   if the one or more non-conformities are not resolvable, then acquiring a new reference spectrum.

14. The measurement apparatus of claim 13, wherein said determining the acceptability of the pre-existing reference spectrum or of the modified pre-existing reference spectrum further includes instructions, criteria and code segments for evaluating each non-conformity so as to determine if any of the non-conformities corresponds to a simple spectral artifact and for those non-conformities categorized as being a simple spectral artifact taking no action to correct for such simple spectral artifacts.

15. The measurement apparatus of claim 13, wherein said instructions, criteria and code segments are such as to further perform the method step(s) of storing one or more spectral shapes that are associated with one or more given spectral effects; and wherein said resolving further includes instructions, criteria and code segments for comparing the one or more stored spectral shapes with the identified one or more non-conformities to determine a relationship between a given stored spectral shape and a particular non-conformity; and if a relationship is determined, using the stored spectral shape to determine a corrective action to resolve the non-conformity.

16. The measurement apparatus of claim 13, wherein said instructions, criteria and code segments are such as to further perform the method steps of storing other spectral information and wherein said determining the acceptability of the pre-existing reference spectrum or of the modified pre-existing reference spectrum further includes instructions, criteria and code segments for evaluating each non-conformity with the other spectral information to determine if the other information relates to the non-conformity and the resolution of the non-conformity and if it is determined that the other information relates, then applying a corrective action related to the other information to resolve the non-conformity.

17. The measurement apparatus of claim 13, wherein said determining if the non-conformities are resolvable further includes instructions, criteria and code segments for:
   comparing spectrums for each of a present scan and the pre-existing reference spectrum to identify the spectral region(s) exhibiting a non-conformity;
   comparing each identified non-conformity with saved spectral information to determine if the non-conformity is one of environment related, instrument related or spectral related;
   determining if the non-conformity with the pre-existing reference spectrum is resolvable by adjusting the pre-existing spectrum on the saved information and the present reference scan;
   if said determining determines that the pre-existing reference spectrum is resolvable, adjusting the pre-existing reference spectrum to create the modified pre-existing reference spectrum.

18. The measurement apparatus of claim 13, wherein the spectroscopy technique embodies an ATR interface and wherein said determining the acceptability of the pre-existing reference or of the modified pre-existing reference spectrum further includes instructions, criteria and code segments for evaluating the one or more non-conformities to determine if one or more non-conformities are indicators of a dirty ATR interface; and if determined as being a dirty interface providing an indication to clean the interface.

19. The measurement apparatus of claim 18, wherein after cleaning of the interface, repeating said steps of acquiring, comparing and determining to determine if the ATR interface is clean.

20. The measurement apparatus of claim 18, wherein after cleaning the interface and repeating said determining if one or more non-conformities are indicators of a dirty ATR interface, determining if this is the first time such a determination is being made, and if it is determined that this is not the first time, causing the process to proceed to acquiring a new reference sample and thereafter acquiring the one or more scans of the sample.

21. The measurement apparatus of claim 13, wherein said instructions, criteria and code segments are such as to further perform the method steps of:
   before acquiring the sample spectrum, providing a message that instructs the user to take the actions involved with acquiring the sample spectrum; and
   after acquiring the sample spectrum, analyzing the sample scan(s) in conjunction with one of the pre-existing background reference spectrum or the modified pre-existing reference spectrum so as to yield a corrected sample spectrum.

22. The measurement apparatus of claim 21, wherein said instructions, criteria and code segments are such as to further perform the method step(s) of, after said analyzing is performed, providing results of such analyzing to the user.

23. The measurement apparatus of claim 21, wherein said providing further includes instructions, criteria and code segments for displaying the results to the user.

24. The measurement apparatus of claim 13, wherein said determining one of acceptability of the pre-existing reference spectrum or of a modified pre-existing reference spectrum is performed before acquiring the one or more scans of the sample.

25. A non-transitory computer medium on which is stored an applications program for execution on a logic circuit including a digital processor or microprocessor; such an applications program including instructions, criteria and code segments for performing a methodology including the steps of:
   determining if there is a pre-existing reference spectrum available;
   acquiring one or more scans of a sample of interest;
   determining one of acceptability of the pre-existing reference spectrum or of a modified pre-existing reference spectrum either (a) before acquiring the one or more scans of the sample or (b) after acquiring the one or more scans of the sample;
   wherein said determining the acceptability of the pre-existing reference spectrum or of the modified pre-existing reference spectrum includes:
   acquiring a present reference scan;
   comparing the present reference scan and the pre-existing reference spectrum to determine if there are any non-conformities there between;
   if one or more non-conformities are found between the present reference scan and the pre-existing reference spectrum, determining if the one or more non-conformities are resolvable or not;
   if the one or more non-conformities are resolvable; resolving each non-conformity in a manner determined to resolve the one or more non-conformities; and
   if the one or more non-conformities are not resolvable, then acquiring a new reference spectrum.

26. The non-transitory computer medium of claim 25, wherein said determining one of acceptability of the pre-existing reference spectrum or of the modified pre-existing reference spectrum is performed before acquiring the one or more scans of the sample.

27. The non-transitory computer medium of claim 25, wherein said determining one of acceptability of the pre-existing reference spectrum or of a modified pre-existing reference spectrum further includes instructions, criteria and code segments for evaluating each non-conformity so as to determine if any of the non-conformities corresponds to a simple spectral artifact and for those non-conformities categorized as being a simple spectral artifact taking no action to compensate for such simple spectral artifacts.

28. The non-transitory computer medium of claim 26, wherein said determining one of acceptability of the pre-existing reference spectrum or of a modified pre-existing reference spectrum further includes instructions, criteria and code segments for evaluating each non-conformity so as to determine if any of the non-conformities corresponds to a simple spectral artifact and for those non-conformities categorized as being a simple spectral artifact taking no action to compensate for such simple spectral artifacts.

29. The non-transitory computer medium of claim 25, wherein said instructions, criteria and code segments are such as to further perform the method step(s) of storing one or more spectral shapes that are associated with one or more given spectral effects; and wherein said resolving further includes instructions, criteria and code segments for comparing the one or more stored spectral shapes with the identified one or more non-conformities to determine a relationship between a given stored spectral shape and a particular non-conformity; and if a relationship is determined, using the stored spectral shape to determine a corrective action to resolve the non-conformity.

30. The non-transitory computer medium of claim 26, wherein said instructions, criteria and code segments are such as to further perform the method step(s) of storing one or more spectral shapes that are associated with one or more given spectral effects; and wherein said resolving further includes instructions, criteria and code segments for comparing the one or more stored spectral shapes with the identified one or more non-conformities to determine a relationship between a given stored spectral shape and a particular non-conformity; and if a relationship is determined, using the stored spectral shape to determine a corrective action to resolve the non-conformity.

31. The non-transitory computer medium of claim 25, wherein said instructions, criteria and code segments are such as to further perform the method steps of storing other spectral information and wherein said resolving further includes instructions, criteria and code segments for evaluating each non-conformity with the other spectral information to determine if the other information relates to the non-conformity and the resolution of the non-conformity and if it is determined that the other information relates, then applying a corrective action related to the other information to resolve the non-conformity.

32. The non-transitory computer medium of claim 26, wherein said instructions, criteria and code segments are such as to further perform the method steps of storing other spectral information and wherein said resolving further includes instructions, criteria and code segments for evaluating each non-conformity with the other spectral information to determine if the other information relates to the non-conformity and the resolution of the non-conformity and if it is determined that the other information relates, then applying a corrective action related to the other information to resolve the non-conformity.

33. The non-transitory computer medium of claim 25, wherein said determining if the non-conformities are resolvable further includes instructions, criteria and code segments for:

comparing spectrums for each of a present scan and the pre-existing reference spectrum to identify the spectral region(s) exhibiting a non-conformity;
  comparing each identified non-conformity with saved spectral information to determine if the non-conformity is one of environment related, instrument related or spectral related;
  determining if the non-conformity with the pre-existing reference spectrum is resolvable by adjusting the pre-existing spectrum based on the saved information and the present reference scan;
  if said determining determines that the pre-existing reference spectrum is resolvable, adjusting the pre-existing reference spectrum.

34. The non-transitory computer medium of claim 26, wherein said determining if the non-conformities are resolvable further includes instructions, criteria and code segments for:

comparing spectrums for each of a present scan and the pre-existing reference spectrum to identify the spectral region(s) exhibiting a non-conformity;
  comparing each identified non-conformity with saved spectral information to determine if the non-conformity is one of environment related, instrument related or spectral related;
  determining if the non-conformity with the pre-existing reference spectrum is resolvable by adjusting the pre-existing spectrum based on the saved information and the present reference scan;
  if said determining determines that the pre-existing reference spectrum is resolvable, adjusting the pre-existing reference spectrum.

\* \* \* \* \*